United States Patent [19]
Batten et al.

[11] Patent Number: 5,398,690
[45] Date of Patent: Mar. 21, 1995

[54] SLAVED BIOPSY DEVICE, ANALYSIS APPARATUS, AND PROCESS

[76] Inventors: Bobby G. Batten, 255 Archer's Mead, Williamsburg, Va. 23185; John A. Companion, 20A Curtis La., Hampton, Va. 23669

[21] Appl. No.: 285,397
[22] Filed: Aug. 3, 1994
[51] Int. Cl.$^6$ .............................................. A61B 8/12
[52] U.S. Cl. .......................... 128/662.05; 128/662.06; 128/660.03
[58] Field of Search ...................... 128/660.03, 662.03, 128/662.05, 662.06

[56] References Cited

U.S. PATENT DOCUMENTS

| | | | |
|---|---|---|---|
| 5,090,414 | 2/1992 | Takano | 128/662.06 |
| 5,178,148 | 1/1993 | Lacoste et al. | 128/662.06 |
| 5,282,472 | 2/1994 | Companion | 128/662.06 |
| 5,335,663 | 8/1994 | Oakley et al. | 128/662.05 |

*Primary Examiner*—George Manuel
*Attorney, Agent, or Firm*—Wallace J. Nelson

[57] ABSTRACT

A computer controlled rectal biopsy probe is employed to receive an ultrasonic signal from an ultrasonic transmitter which may be carried by a prior art urethral examination and mapping probe. The mapping probe signal is employed by the biopsy probe to position a biopsy needle within the rectal wall in alignment with a suspect prostate tumor detected by the mapping probe. The biopsy needle is computer controlled to penetrate the rectal wall, extend into the center of the suspect tumor, and cut a tissue sample therefrom. The tissue sample is removed through the rectal probe, to an analysis station, without removal of the rectal probe. If found malignant, suitable treatment (medical, radiation or surgical) may be directly applied to the tumor through the rectal probe. Computer analysis of the tissue sample may be performed by optical analysis or by ultrasonic density examination apparatus.

26 Claims, 19 Drawing Sheets

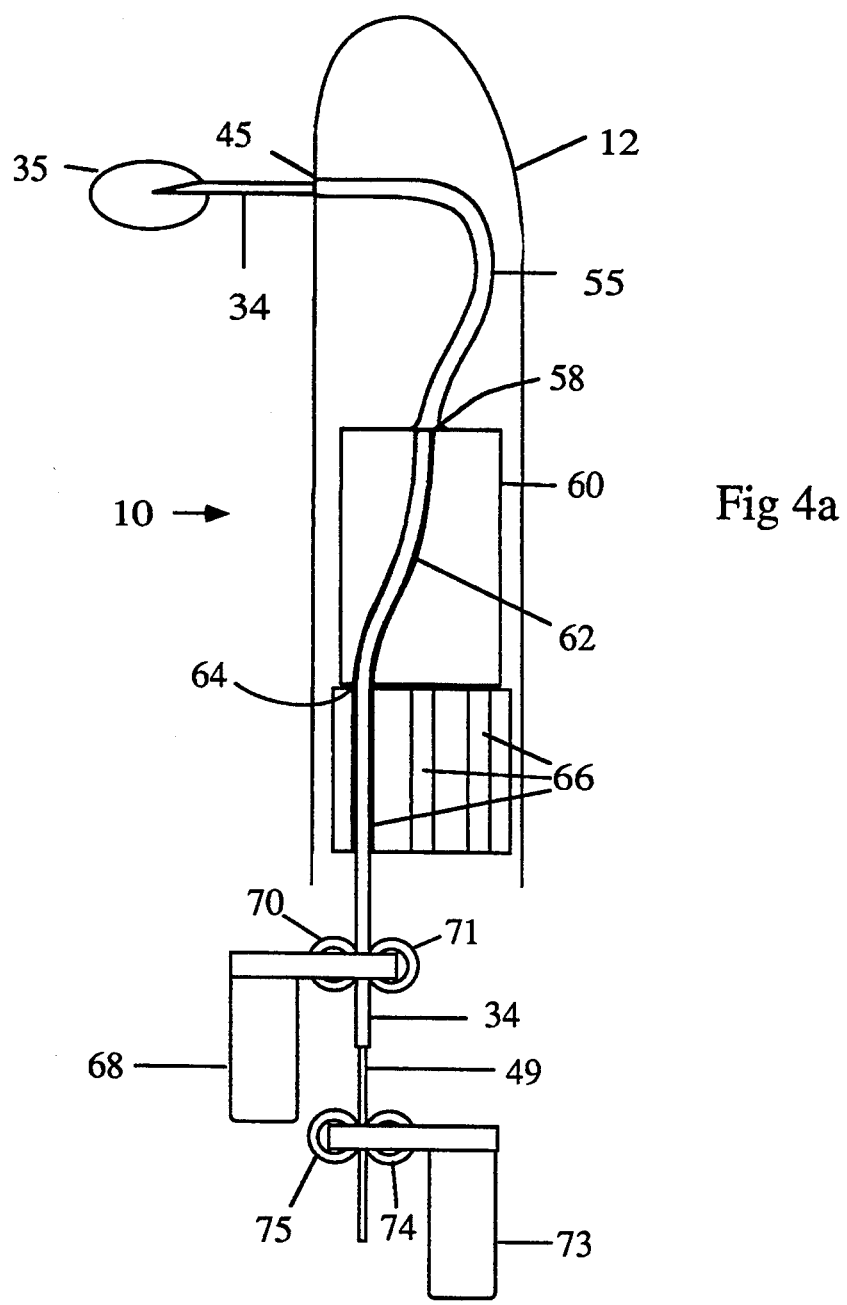
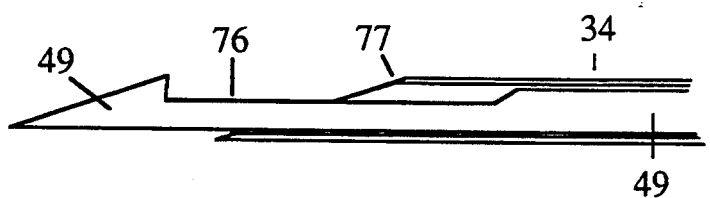

SLAVED BIOPSY DEVICE, ANALYSIS APPARATUS, AND PROCESS

FIELD OF THE INVENTION

This invention relates generally to medical instrumentation and relates specifically to a slaved biopsy device for obtaining tissue samples from a prostate tumor, the apparatus and process for analyzing same, and a device and process for treatment of prostate cancer with several techniques utilizing the slaved biopsy device as a means of internal application of these techniques.

BACKGROUND OF THE INVENTION

A prostate examination and treatment system and process is disclosed in applicants' U.S. Pat. No. 5,282,472. The present invention is specifically designed for and intended for use with this patented system and process, which is incorporated herein by reference. In one aspect of this patented invention, an ultrasonic system is employed for detecting, identifying and precisely locating tumors in the prostate gland of a patient. Once a tumor is positively located and identified, it is essential to obtain a biopsy thereof to confirm the need of, or to assist in the decision of what operative or treatment procedures should be employed. The practice of the present invention is not limited to use with the patented system but is deemed operable with any ultrasonic prostate tumor detecting system.

Present procedures for obtaining a biopsy of prostate tumors frequently are painful, result in frequent false negative results, and frequent infections that hinder the healing process.

Accordingly, it is an object of the present invention to provide an improved system for obtaining a prostate biopsy tissue sample.

Another object of the present invention is to provide a prostate biopsy tissue sample taking system that ensures that the tissue sample taken is removed from the center of the suspected tumor.

A further object of the present invention is a system for taking a biopsy tissue sample from within an area identified as a tumor by an ultrasonic urethral prostate examination probe.

An additional object of the present invention is to provide a biopsy system that is guided and aimed under the control of the same data acquisition computer employed to locate and define a tumor of the prostate.

An additional object of the present invention is to provide a biopsy needle aimed by a computer under the direction of an operating physician to ensure accuracy of the deployment of the biopsy needle into an identified tumor.

A still further object of the present invention is to provide a system for extruding a biopsy needle into the computed center of a defined tumor on a defined geometrical path to ensure absolute accuracy in obtaining the tissue sample.

Another object of the present invention is a biopsy system that provides verification and absolute control to the operating physician in positioning the biopsy needle.

Another object of the present invention is to provide a system and process whereby a tumor tissue sample taken by a biopsy needle can be removed from the patient for examination and, if malignancy is indicated, the biopsy needle can be replaced by a conduit for the introduction of various treatment modalities such as, thermal, surgical, radiological, high energy, cryogenics, or other methods, to thereby provide a system to treat or destroy the tumor without the need for surgical-removal of the prostate.

A further object of the present invention is to provide a biopsy needle system that includes the ability to optically inspect, seal the exit wound, and disinfect the rectal wall at the point of biopsy needle penetration to thereby minimize the occurrence of secondary infection.

A further object of the present invention is to provide a biopsy needle system that permits the insertion of a fiber optic light to illuminate the tumor tissue and thereby facilitate malignancy determination thereof.

SUMMARY OF THE INVENTION

According to one aspect of the present invention, the foregoing and additional objects are attained by employing an ultrasonic, prostate tumor, detecting device, such as the patented, computer controlled, ultrasonic mapping probe referred to hereinbefore. In this patented system, the ultrasonic probe is inserted within the urethra of a patient to map the urethral area and to determine the existence, and pin-point the location, of any tumor present in the prostate capsule.

Once the tumor is located and indicated on the computer screen by this patented system, a rotatable, slaved, biopsy probe is inserted into the patient's rectum under the control of the same computer system. The biopsy probe is provided with a gimbaled tip end portion thereon that houses an ultrasonic receiver for detecting the ultrasonic energy being emitted through the prostate and directed to the tumor therein. The computer controls permit controlled rotation of the biopsy probe and vertical tilting of the gimbaled tip thereon to enable (via interaction with the computer display) precise alignment of the central axis of the ultrasonic receiver on the anal probe, with the tumor in the prostate. The detected ultrasonic energy comprises that particular scan disk emanating from the prostate examination and mapping probe transducer, of the patented system, which intersects the tumor location. The slaved biopsy device of the present invention employs a beam finding mechanism (ultrasonic receiver) to ensure an accurate alignment of the vector of the biopsy needle carried by the biopsy probe with the plane of the ultrasonic scan.

The slaved biopsy probe of the present invention is employed to align a biopsy needle carried concentrically to the axis of the ultrasonic receiver mounted therein, with the detected tumor, utilizing the same ultrasonic signals, and computer system, as that of the urethral probe. Once the biopsy probe is properly aligned with the detected tumor, a biopsy needle is extended from the probe, through the rectal wall, into the center of the detected tumor, and a biopsy tissue sample extracted therefrom.

This biopsy tissue sample is removed and analyzed while retaining the slaved biopsy probe intact for the insertion of appropriate treatment structure, which can include various treatment modalities such as, thermal, surgical, chemical, radiological, high energy and cryogenics, or other methods. Suitable pores are provided in the end of the probe to dispense a lubricant and an anesthetic during probe insertion into the rectum. As withdrawn, an antiseptic cleanser washes down the area of biopsy needle penetration and the opening caused thereby the rectal wall is sealed.

BRIEF DESCRIPTION OF THE DRAWINGS

A more complete appreciation of the invention and many of the attendant advantages thereof will be better understood when considered in connection with the accompanying drawings wherein:

FIG. 4a is a part sectional, part schematic, view of the needle retracting mechanism that also provides access to the patient for tumor treatment without removal of the slaved biopsy probe from the patient;

FIG. 4b is a part sectional, part schematic, illustration of one needle cutting mechanism for taking a biopsy of a tumor within the prostate of a patient;

FIG. 5b is an enlarged schematic view of the biopsy needle dispenser employed in the embodiment illustrated in FIG. 5a;

FIG. 5c is a perspective view of the needle tip employed in the biopsy needle shown in FIG. 5a;

FIG. 5d is a sectional view of the biopsy needle as taken along line V—V of FIG. 5a;

FIG. 6b is an illustration of the sequence of cutting action performed by the biopsy needle shown in FIG. 6a;

FIG. 9 is a part sectional, part schematic, view of an alternate sample analysis system for analyzing the cut tumor tissue sample.

DETAILED DESCRIPTION

Figure 1:
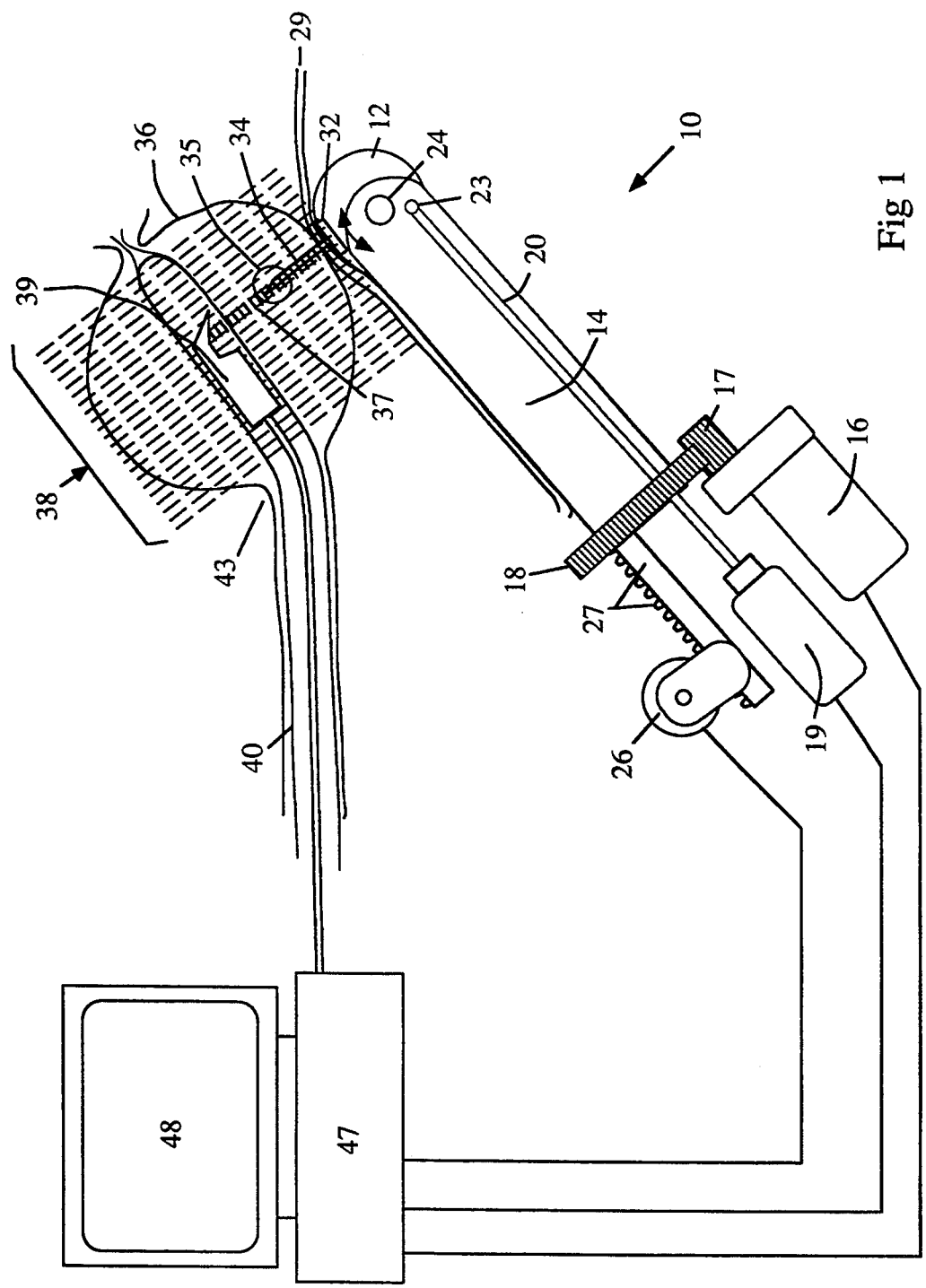
FIG. 1 is a schematic, part sectional, view of the slaved biopsy probe of the present invention, and instrumentation therefor, as employed with the referenced patented, ultrasonic, urethral, mapping probe.
Figure 2:
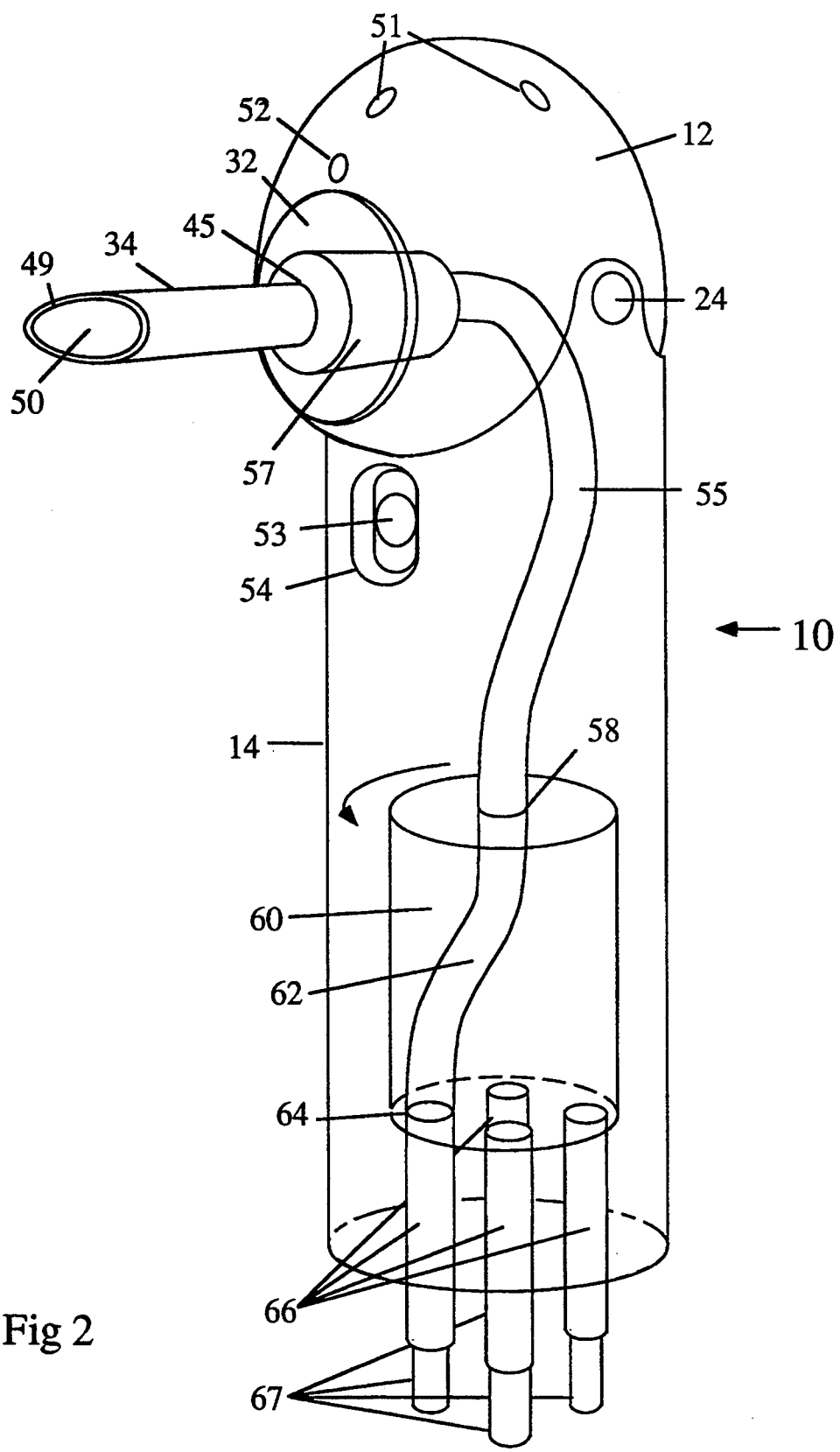
FIG. 2 is an enlarged, part schematic, part sectional, view of the slaved biopsy probe shown in FIG. 1.

Referring now to the drawings, and more particularly to FIGS. 1 and 2, the slaved biopsy device of the present invention is shown and designated generally by reference numeral 10. Biopsy probe 10 is provided with a gimbaled head portion 12, and an elongated shaft portion 14. The aft end of probe 10 is gear connected to a stepper motor 16 via gears 17, 18 to effect controlled rotation of the probe, as will be further explained hereinafter. A motor 19 serves to provide a push/pull action to a rigid shaft 20 connected at one end thereto. The other end of shaft 20 is secured to a pin 23 on gimbaled head 12 to effect pivotal movement thereof about pivot pin 24 to thereby adjust the vertical angle of gimbaled head 12 to that desired, as will also be further explained hereinafter. An additional stepper motor 26 is geared to linear gear teeth 27, disposed over a portion of the length of probe shaft 14, and serves to insert and withdraw probe 10 within (and from) rectum 29 of a patient, as will also be further explained hereinafter.

An ultrasonic receiver 32 is carried by gimbaled head 12 and surrounds a biopsy needle 34. As schematically shown, biopsy needle 34 is employed to penetrate and extract a tissue sample from a tumor 35 that is located within the prostate capsule 36 of a patient. Biopsy needle 34 is aligned with the tumor 35 by focalizing on ultrasonic beam 37 by ultrasonic receiver 32. Ultrasonic beam 37 is obtained as part of the scan pattern 38 emitted by rotating ultrasonic transducer 39 carried by urethral mapping probe 40.

The entire operation of urethral mapping probe 40, and the slaved biopsy probe assembly 10 is controlled by an attending physician, or other medical personnel, through a data acquisition computer and control assembly 47. The movement and actions of mapping probe 40 and the slaved biopsy probe 10, including the action of biopsy needle 34, is visible to, and monitored by the attending medical personnel operator via computer display screen 48, as will be further described hereinafter.

Figure 3A:
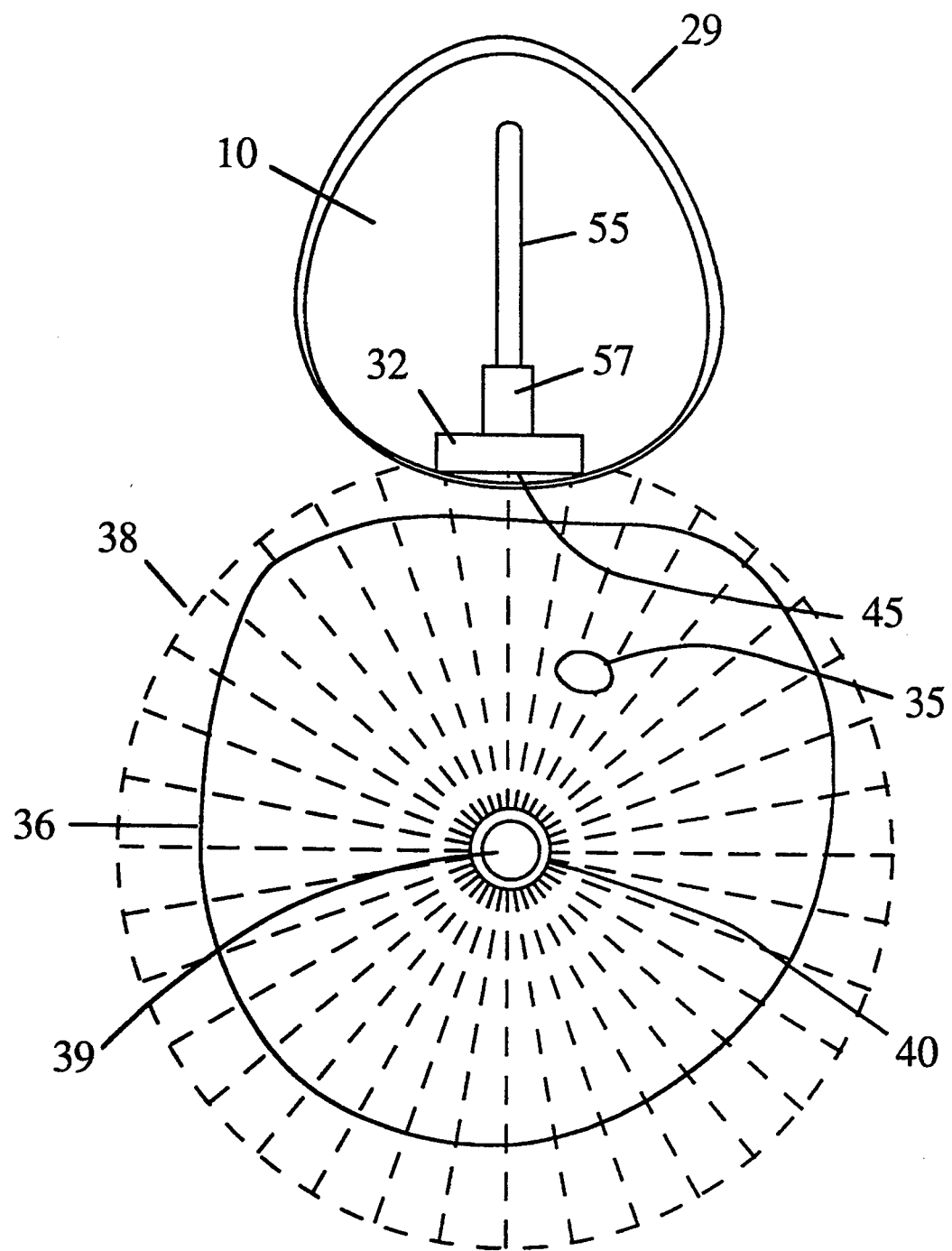
FIG. 3a is a schematic, sectional, anatomical view of a diseased prostate showing a tumor therein and the ultrasonic detection pattern from an ultrasonic urethral probe and the biopsy probe disposed within the patient's rectum.
Figure 3B:
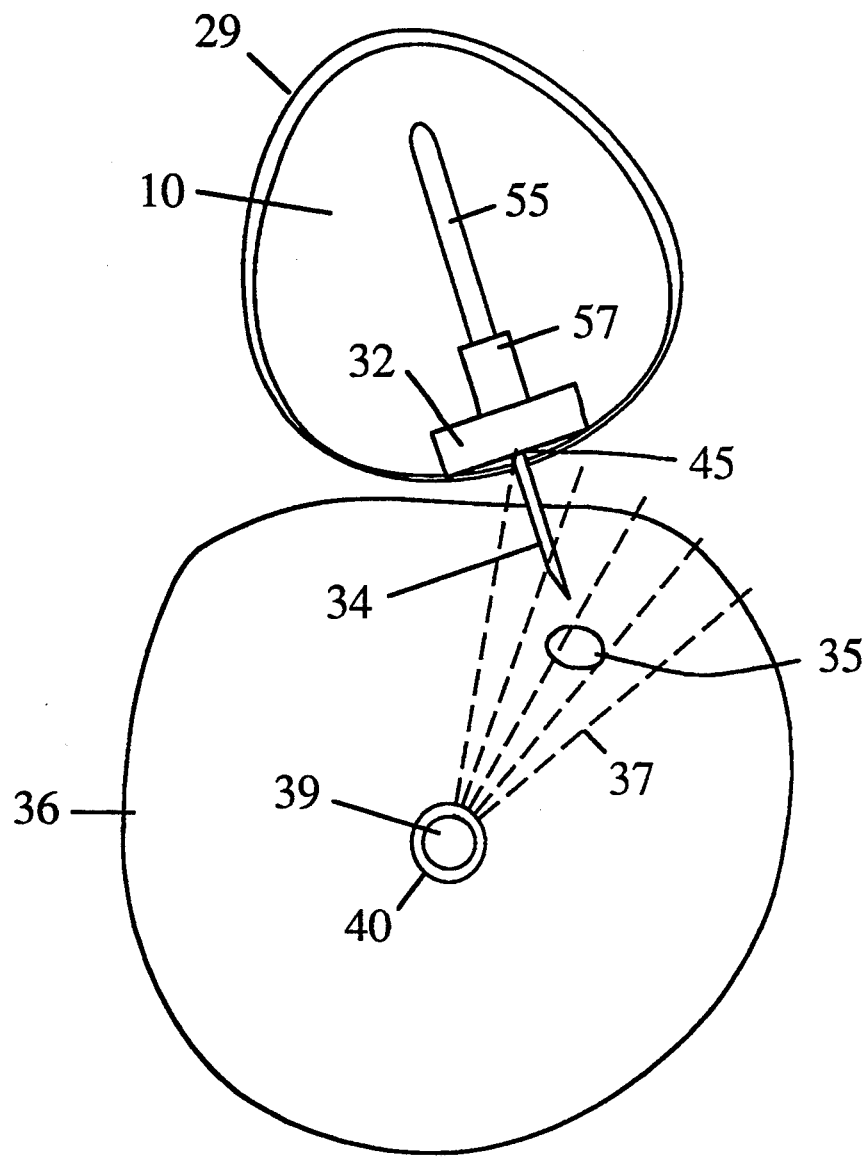
FIG. 3b is similar to FIG. 3a and illustrates the positioning of the biopsy needle to penetrate and take a sample tissue from the tumor.

The step and rotating scan function of the patented system generates a series of ultrasonic beams in a pattern resembling spokes on a bicycle wheel, as schematically shown in FIG. 3a and designated by reference numeral 38. The hub of the wheel pattern 38 is centered on the urethra because the ultrasonic transducer 39 is rotating as it moves through the prostatic urethra 41 inside the probe tube 40 (FIG. 1) for examination and mapping thereof. The scan pattern 38 (FIG. 1) may be visualized as a stack of bicycle wheels, where each wheel represents one axial step of the transducer 39, and the spokes represent the rotating pulsed ultrasound beam as it scans each circular portion of prostatic tissue.

In order to geometrically align the vector which will correctly place the tip of biopsy needle 34 into the center of an identified tumor 35, that vector must be congruent with the plane of the scan wheel, or disk, which intersects the center of the tumor 35.

Since the rectum 29 (FIG. 3) lies behind and adjacent to the prostate 36, as the ultrasound beam traverses that portion of the prostate 36 that lies between the urethra and the rectum, this beam will be detectable to ultrasonic receiver 32 positioned within the rectum 29 of the patient. The lumen of biopsy needle 34 (FIG. 2) is filled with a retractable plug 49 having a tip end in the shape of a convex wedge 50. Wedge tip 50 acts as an effective ultrasonic reflector in the approach mode of needle insertion to give visual feedback to the physician, to ensure an accurate alignment of the ultrasonic scan wheel.

Further description of the retractable tip 49 and the function for ultrasonic reflector 50 will be given hereinafter. The need for ultrasonic receiver 32 and ultrasonic reflector 50 is due to the fact that the prostate examination and mapping probe 40 flexes to accommodate itself to the natural bend 43 where the urethra exits the penis and enters prostatic capsule 36. Therefore, the angle of the axis of the examination and mapping probe 40, and thus the plane of the scan wheel, which is at right angles to that axis, is a variable.

Referring more particular to FIG. 2, gimbaled head 12 of slaved biopsy probe 10 includes a series of ports 51 for dispensing lubricant and an anesthetic therethrough to lubricate rectal wall 29 and thereby reduce, or minimize, the risk of infection and patient discomfort during insertion and removal of probe 10. Ports 51 are connected through suitable conduits extending the length of slaved biopsy probe 10 to suitable lubricant and anesthetic reservoirs at the base of the probe. These conduits and reservoirs are not illustrated in the drawings, or further described herein, in the interest of brevity and clarity. An additional port 52 is provided in gimbaled head 12 of slaved biopsy probe 10 and serves to dispense a suitable antiseptic cleanser (from a suitable source, also not shown) to wash down the area in rectal wall 29 through which the biopsy needle 34 will penetrate.

An optical pick-up 53, recessed in a depression 54 in the sidewall of probe shaft 14, permits physician monitoring of the biopsy probe placement and retrieval. The recessed placement of optical pick-up is necessary to provide focal length clearance between the lens and the rectal wall 29. Visual images obtained by optical pick-up 53 are displayed on the control computer screen 48. A "Fuzzy Logic" control program within computer 47 uses a signal strength maximization, feedback program with the signal strength of the ultrasonic signal received by the ultrasonic receiver element 32 as the source. There are three separate mechanical movements involved in aligning slaved biopsy probe 10 with the detected tumor 35 (FIG. 3). The first is an axial movement of the entire probe portion to bring the portal 45, through which biopsy needle 34 emerges through the side of the slaved biopsy probe gimbaled end 12, to a position immediately adjacent to the periphery of the scan plane 37 containing the identified tumor 35. This movement is provided by a stepper motor assembly 26 initiated by the operating medical personnel and then governed by a signal strength feedback computer program in the computer controls and computer 47.

The second movement then aligns the vector of the biopsy needle extrusion with the plane of the scan disk 37 (FIG. 1) regardless of the angle of that scan disk to the slaved biopsy probe shaft 14. The ultrasonic receiver element 32, as discussed hereinbefore, is annular in shape and is concentrically located around the biopsy needle exit portal 45 on gimbaled end 12. The vertical angle of the gimbaled end 12 is determined by the output of the "Fuzzy Logic" control program and set at the determined location via motor 19 and shaft actuator 20. This actuator manipulates the vertical angle of gimbaled end 12 to provide perfect alignment of the ultrasonic receiver 32 and biopsy needle exit portal 45 mounted thereon, with the plane of the scan disk (FIG. 3). Since biopsy needle 34 is extruded through port 45 in a straight line, perpendicular to and from the center of the plane of the ultrasonic receiver element 32, it is perfectly aligned with the plane of the scan disk 37 in which the identified tumor 35 is located.

An indication is then presented to the operating physician on the computer screen 48 that the alignment is correct. At this time, the physician places the on screen cursor on the exact point within the scan disk where it is desired to take the biopsy. The computer system 47 will them compute the radial angle and the depth of penetration which will place the tip of the biopsy needle 34 in the exact center of the identified tumor 35 when it is extruded.

In the third mechanical movement, stepper motor 16 rotates the body of the slaved biopsy probe 10, and thus the exit portal 45, to the correct angle (FIG. 3b) within the patient's rectum, under the control of computer 47.

Biopsy needle 34, in the preferred embodiment illustrated in FIG. 2, is in the form of a tube of memory material (metal, plastic or composite), which moves within the slaved biopsy probe 10 in a curved, tubular, flexible passageway 55. Passageway 55 holds the memory material tubular needle 34 in the curved shape to permit it to fit inside the dimensions of the slaved biopsy probe 10 when the needle is in the retracted position. The distal end of passageway 55 is attached to the needle exit portal 45.

Figure 3C:
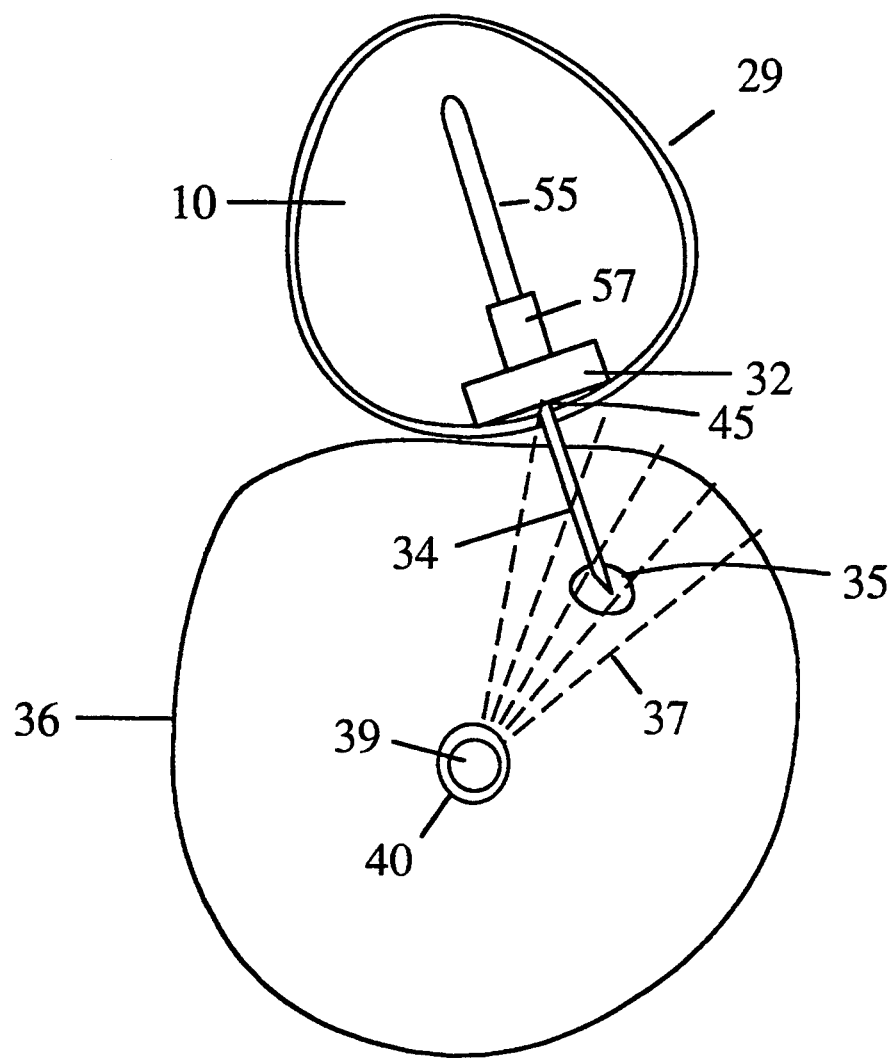
FIG. 3c is similar to FIG. 3b and shows the biopsy needle contacting the tumor.

Immediately before arriving at exit portal 45, passageway 55 passes through an encircling tubular heating element 57 (FIG. 2). When the operating physician commands the biopsy to be taken, the memory material needle tube 34 is pushed out of the orifice of passageway 55 and through exit portal 45. As needle 34 emerges, it is heated via heating element 57 causing the tubular needle to straighten and stiffen. Biopsy needle 34 is then extruded in a straight line to the point of intersection with the computed position of the suspected tumor 35 (FIG. 3c). As described hereinbefore, to ensure that the tissue sample may only be taken at the point of interest, the lumen of needle tube 34 is filled with retractable plug 49. The slightly convex wedge face 50, of retractable plug 49, acts as the penetrating point of biopsy needle 34 during insertion, and also acts as an effective ultrasonic reflector in the approach mode of the insertion to give visual, positional feedback to the physician.

Thus, once the ultrasonic system within the prostate examination and mapping probe 40 (FIG. 1) has computed the coordinates for the destination point of the biopsy needle tube 34, it then switches into a narrow angle scan mode 37 (FIG. 3b) covering the expected approach path of biopsy needle tube 34. This enables the physician to see the approach of the biopsy needle tube 34 to the identified area on the computer screen 48.

Figure 3D:
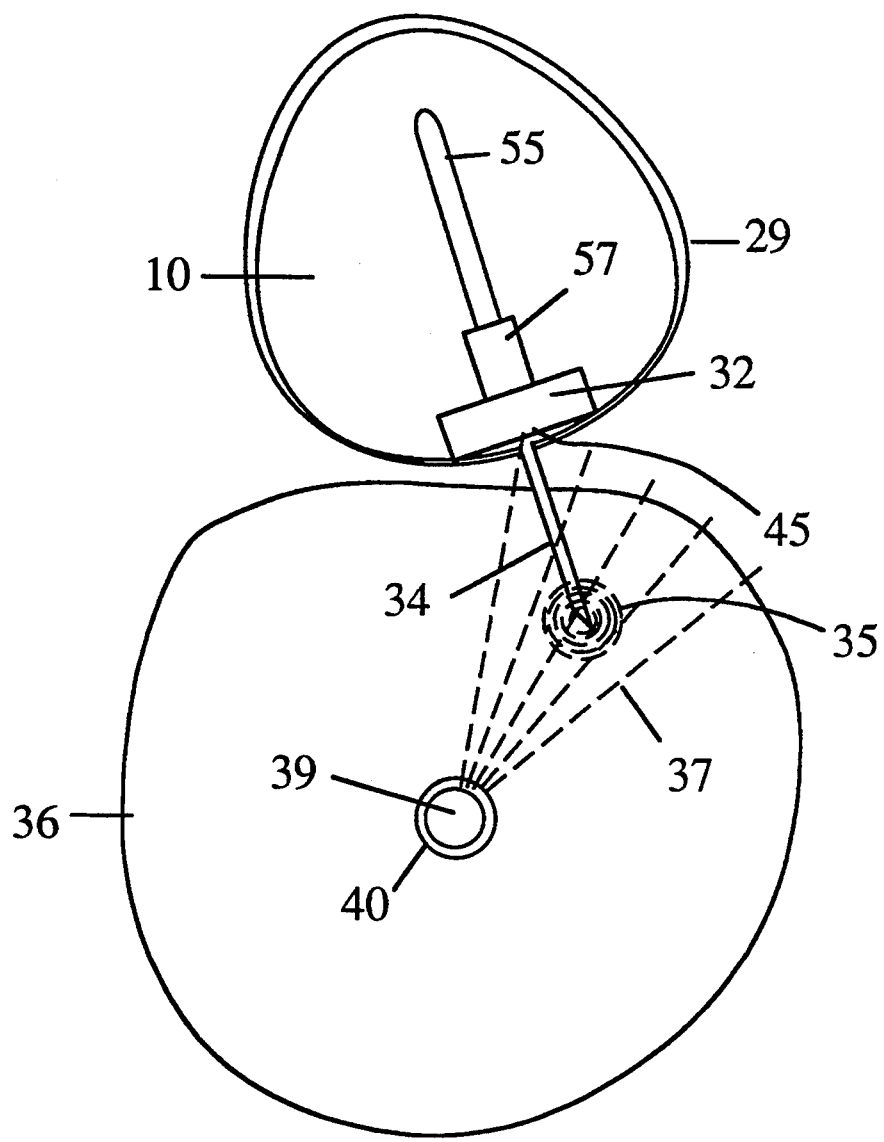
FIG. 3d is similar to FIG. 3c and illustrates the biopsy needle extracting a tissue sample from the center of the detected prostate tumor.

At this point, the physician commands the plug 49 to be withdrawn at the appropriate point in the approach path (optionally, this can be a computer directed function), to permit the biopsy needle tube 34 to cut out a sample of tissue in the principal area of interest (FIG. 3d).

The lower end of instrument passageway 55 (FIG. 2) through which the biopsy needle tube 34 moves, slidably interfaces with a top port 58 located in the top center of a rotary instrument selection cylinder 60. A shallow, S-curve passage 62 extends through cylinder 60 from top port 58 to a bottom port 64 at the base of cylinder 60. The lower port 64 opens near the periphery of the bottom face of cylinder 60, thus providing an off-set interface between the instrument passageway 55 and a group of instrument feed tubes 66. By rotating instrument cylinder 60, the instrument selection passage 62 will connect the upper port 58 with one of the ring of instrument feed tubes 66 which slidably interface with the lower face of cylinder 60. Each of these feed tubes contain a different functional element 67 which can be moved through the instrument selector passage 62 within the instrument selection cylinder 60, through the instrument passageway 55, out of the exit portal 45, and into the identified tumor 35.

The normally selected instrument is the concentric, biopsy needle/wedge plug (34/49) combination. As illustrated in FIG. 4, biopsy needle tube 34 extends through the curved passageway 55, the rotary selector passageway 62, and one of the instrument feed tubes 66 to protrude at its lower end into a drive mechanism including a motor 68 and a capstan/idler wheel assembly 70,71. The capstan/idler wheel 70,71 bears on the outside of the biopsy needle tube 34 to drive it forward into tumor 35, or back, to withdraw needle 34 into it's designated instrument feed tube 66 to clear the way for deployment of other instruments through the passageway 55.

The integral shaft on internal concentric wedge plug 49 extends through the entire lumen of the biopsy needle tube 34 and protrudes past the end thereof for a sufficient distance to engage another drive mechanism consisting of a drive motor 73 and a capstan/idler wheel combination 74,75. Thus, the wedge plug 49 can be moved with the biopsy needle tube 34 forward, or independently backward to clear the end lumen of the biopsy needle tube 34 for the taking of the tissue sample from tumor 35. As shown in FIG. 4b, the actual cutting mechanism of the biopsy needle 32 is essentially the same as is used in conventional biopsy needles. The inner plug 49 is extended forward via its shaft beyond the cutting tip of the biopsy needle within tumor 35 via capstan/idler wheel combination 74,75 to expose a depression 76 behind the tip end thereof. The tumor tissue 35 bulges, or presses, into depression 76 and plug 49 is retraced back into needle 34. This pushes the portion of tumor tissue in depression 76 against the cutting edge 77 of biopsy needle 34, shearing it off. The sheared off tissue remains in depression 76 and is carried, with plug 49, back though needle 34, curved passageway 55, rotary instrument cylinder 60 and into a collection area within the designated instrument feed tube 66 from which it can be extracted for examination.

If the tumor 35 is confirmed as malignant, and if the patient is being examined at a relatively early stage of cancer growth, the slaved biopsy probe 10 may be used to provide a pathway, via the instrument selection cylinder 60 and the multiple feed tubes 66 for direct treatment of the condition.

Thus, if the determination is made that the tissue sample is indeed cancerous, the appropriate treatment instrument may be deployed from its designated feed tube 66, through the rotary selector cylinder 60, which has been rotated to a position connecting the selected instrument feed tube and the curved passageway 55. The selected treatment instrument is extended out through port 45 to deliver the selected cancer treatment directly to tumor 35.

A number of modalities could be employed in this manner without removal of biopsy probe 10. For example, the selected treatment instrument could deliver thermal energy, either via a fiber optic laser, or an electric heater, to coagulate the protein of the area and cause local cell necrosis within the tumor. Also, a cryogenic treatment instrument could be deployed through biopsy probe 10 to freeze the tumor. In some patients the tumor size may already be too large for these treatments at the time of the first examination. In that case, the slaved biopsy probe 10 can be used to deliver potent anti-cancer drugs by injection directly into the tumor, as a possible alternative. Also, it is possible to employ a mechanical cutting treatment instrument, similar but smaller than those presently used for trans-urethral resection operations, and inserted through the feed tube mechanism of biopsy probe 10. Each of these tumor treatments should prove to have a much greater rate of success than present methods due to the early detection afforded by the whole system, and would provide other benefits (such as a shorter recovery time, less chance of infection, probable retention of sexual function and fertility) as well, for the patient.

An alternate form of the biopsy needle for the present invention is illustrated in FIGS. 5a–5h. In this embodiment, biopsy needle 78 is an extruded triangular needle formed of three separate, specially formed, ribbons of stainless steel, as designated by reference numerals 80, 81 and 82. Ribbons 80, 81 and 82 are wound onto separate miniature spools 83, 84 and 85 mounted on a support structure (not designated) at 120 degree angles to each other (FIGS. 5a and 5b) within gimbaled head 12 of biopsy probe 10.

Spools 83, 84 and 85 are rotated simultaneously to deploy or retract the respective ribbons 80, 81 and 82. The distal ends of the ribbons extend through a triangular swaging die 87. As the ribbons are deployed from the spools through the swaging die, the specially formed edges lock together, forming a rigid triangular structure that can be extruded through portal 45 from the side of the slaved biopsy probe 10 to the length of ribbon available on the spools. The cross sectional area of the triangular tube 78 (FIG. 5d) approximates a normal biopsy needle. The tip end 79 of this biopsy needle 78 remains formed at all times and resides within the swaging die 87 when the biopsy needle 78 is retracted. A flexible tube 89 is secured within the base structure 60 to connect with a vacuum device (not illustrated). Vacuum is applied through tube 89 for the aspiration of the tissue sample obtained from tumor 35. After the tissue sample is obtained, spools 83, 84 and 85 are rotated in the opposite direction to withdraw the triangular biopsy needle 78 back into the slaved biopsy probe 10. As the structure passes back through the swaging die 87, the ribbons are separated again and are taken back up onto the spools.

Figure 5A:
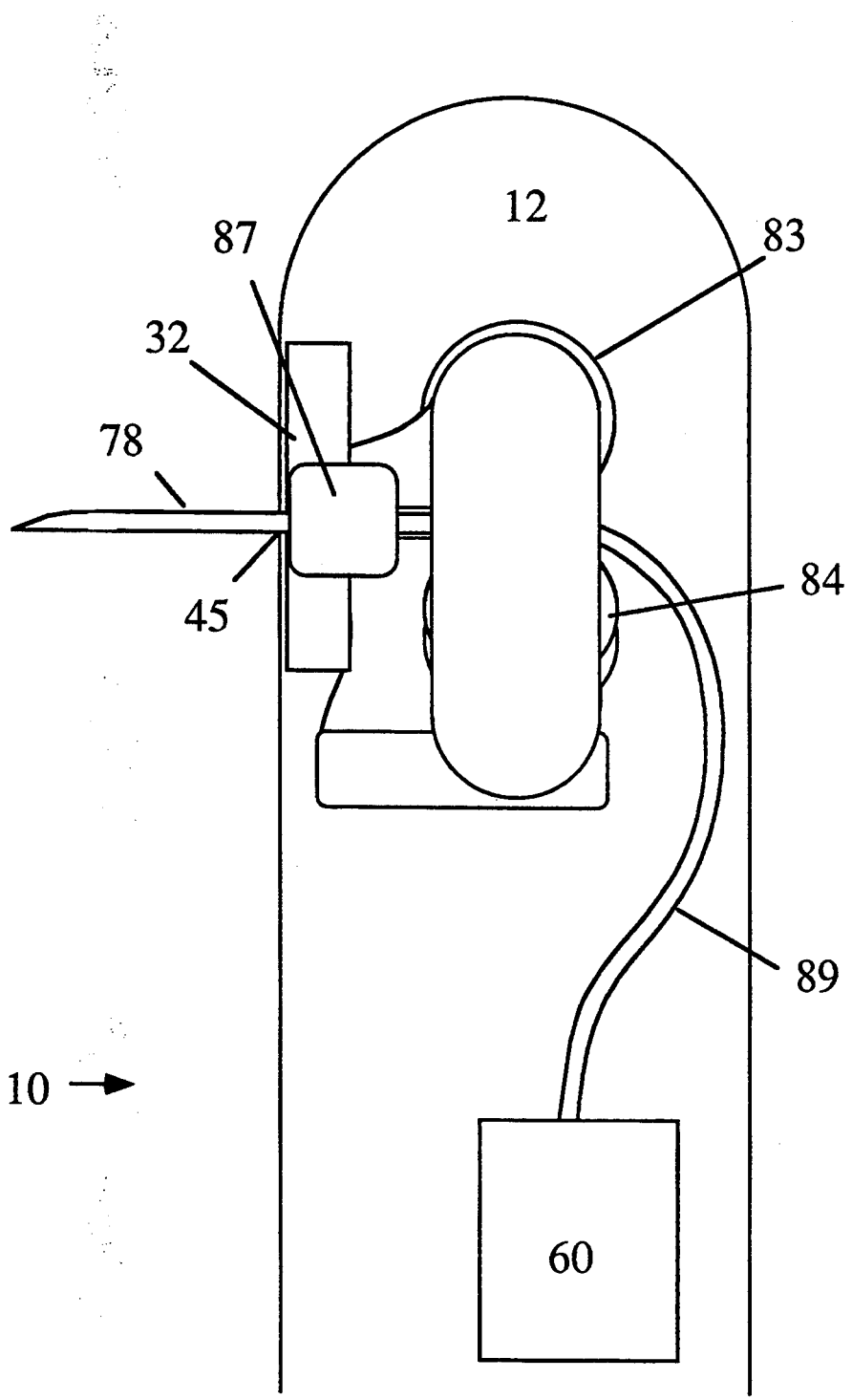
FIG. 5a is a part sectional, part schematic, illustration of an alternate embodiment of the biopsy needle employed in the present invention.
Figure 5B:
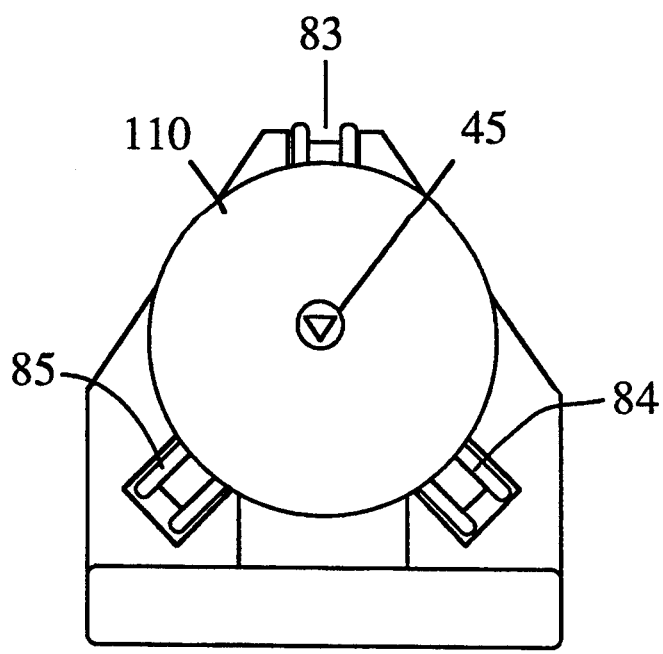
Figure 5C:
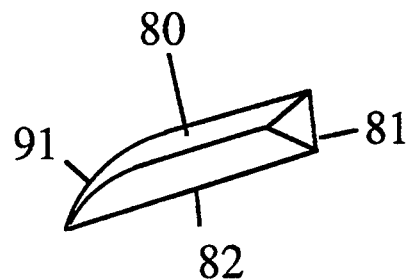
Figure 5D:
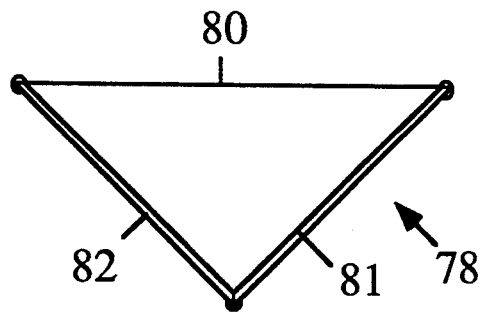
Figure 5E:
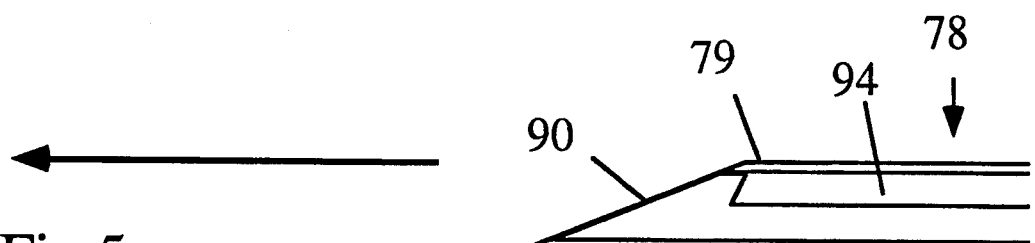
FIGS. 5e-5h are sectional views of the biopsy needle illustrating the sequence of needle tip movement during the taking of a tissue sample from a prostate tumor.
Figure 5F:
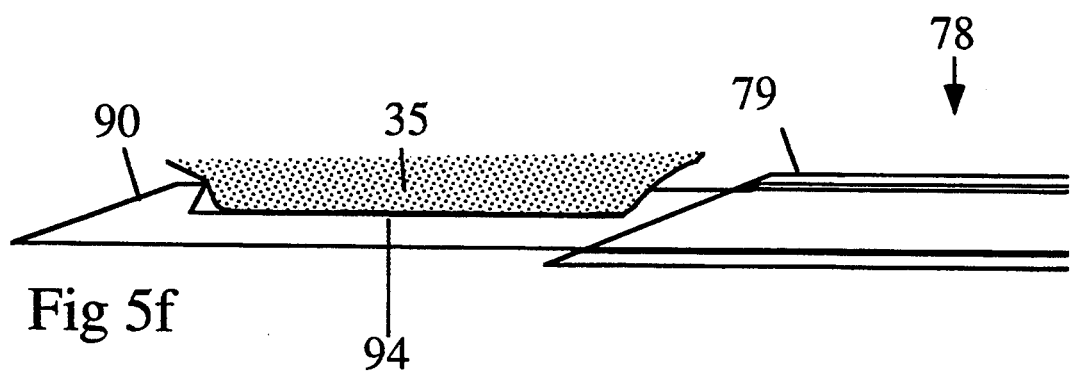
Figure 5G:
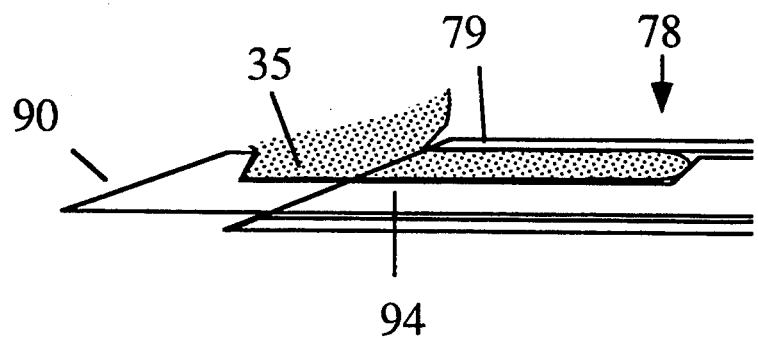
Figure 5H:
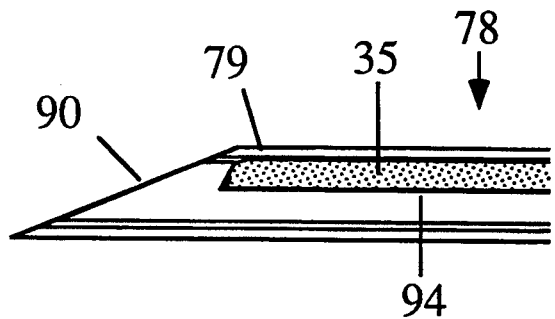

When the three ribbons (80,81,82) are in the retracted position, they are not completely taken up on the spools ((83,84,85) and the leading edge of each ribbon remains within the triangular swaging die 87. In the embodiment described in reference to FIGS. 5a–5h, the ribbon leading edges are welded together so that the cutting end is permanently formed and shaped into a bevel much like that of a conventional biopsy needle. The open tip end 79 of the triangular needle 78 accommodates a concentric cutting plug 90 (FIG. 5e) in the same manner as that described for tip 49 in the standard biopsy needle of FIG. 4b. In operation, the tapered wedge front of the cutting plug 90 forms the cutting face of biopsy needle 78. When the tip 79 of needle 78 reaches the border of the area of interest (tumor 35), the needle deployment is stopped and the cutting plug 90 emerges from the opening of needle 78 (FIG. 5f) and is pushed to the far edge of the area of interest within the tumor 35. As the tip of the cutting plug 90 passes through the tumor 35 tissue, the tissue bulges down into a trough shaped opening 94 behind the head 90. When the desired depth in tumor 35 is reached, the direction of travel of the cutting plug 90 is reversed (FIG. 5g). This pulls the tissue in the trough 94 against the sharp edge of the biopsy needle opening, thus shearing off the tissue in the trough. The cutting plug 90 is retracted through the length of the formed biopsy needle 78 (FIG. 5h) until the tissue bearing trough 94 is adjacent to the opening of flexible vacuum tube 89 for aspiration of the tissue sample.

Another alternate embodiment of the biopsy needle of the present invention is illustrated in FIGS. 6a–6d. This embodiment is similar to that described in reference to FIGS. 5a–5d and like reference numerals are employed for the common parts. In this embodiment, a mechanical shearing action is employed to resect the tissue sample from the area of the suspected tumor 35. The triangular hollow stainless steel needle 78 is formed from three ribbons of stainless steel 80, 81 and 82 extruded from 120 degree angled spools 83, 84 (not visible in this FIG) and 85, as described hereinbefore in reference to FIGS. 5a–5d. One side of the ends of ribbons 81 and 82 are shaped such that they form tapering points, while the end of ribbon 80 is tapered on both sides. Ribbons 81,82 as extended from their respective spools 84 (not illustrated) and 85 are joined along one straight edge thereof. The free edges of ribbons 81, 82 are shaped to form a curved track for the purpose of guiding the separately moveable third side 80. During the process of extruding the biopsy needle 78 through the rectum wall 29, side 80 is fully deployed to form a closed point for needle 78. When the tip of the biopsy needle 78 approaches the identified tumor area, spool 83, carrying ribbon side 80, is stopped momentarily so that it moves backward relative to the other sides 81, 82 thus forming an opening 91 in the tip of biopsy needle 78 (FIG. 6c and the left most illustration of FIG 6b).

The now exposed sharp edges of sides 81, 82 will cut through and enclose a segment of tissue of a length equivalent to the distance between where the opening 91 was activated and the maximum depth of needle penetration. When the biopsy needle probe 78 is stopped at the predetermined point, the side 80 moves forward, cutting through and separating the tissue within the biopsy needle lumen from the rest of the prostate tissue. Biopsy needle probe 78 may then be withdrawn from prostate 35 carrying the tissue sample within itself, or the tissue sample can be aspirated from within the lumen. When the biopsy needle 78 is withdrawn into the slaved biopsy probe 10, the probe itself can be withdrawn from the patient, or treatment can be initiated in the same manner described hereinbefore, followed by the withdrawal of the prostate examination and mapping probe 40 from the urethra.

Figure 6A:
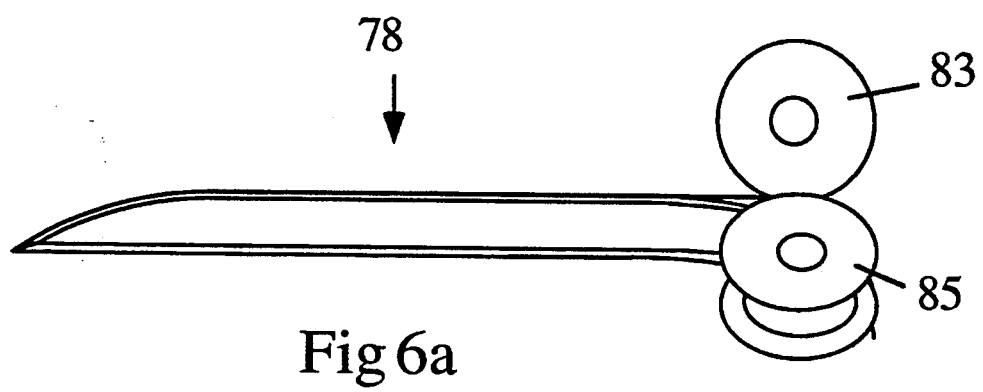
FIG. 6a is a schematic representation of another embodiment of the biopsy needle and needle dispenser system employed in the slaved biopsy system of the present invention.
Figure 6B:
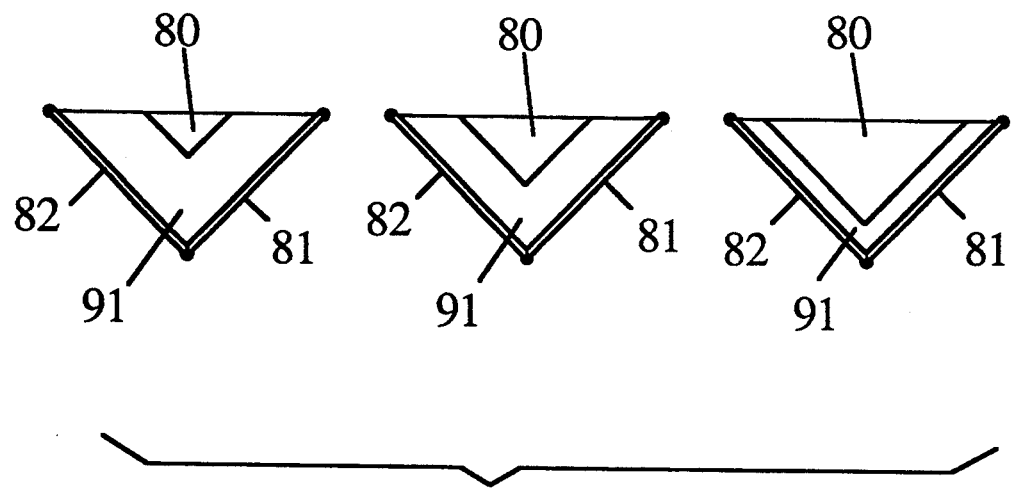
Figure 6C:
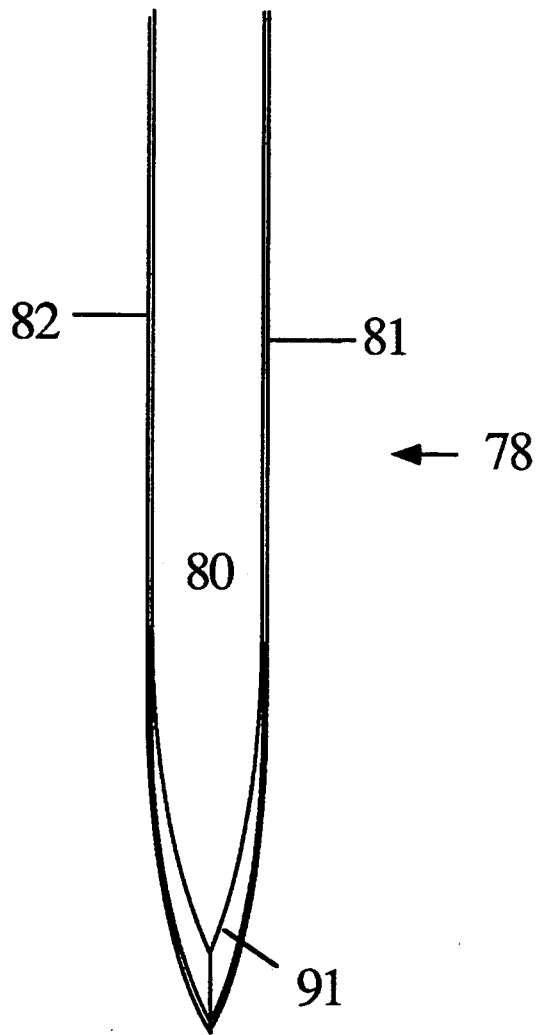
FIG. 6c is a top perspective of the biopsy needle shown in FIG. 6a during a cutting procedure.

FIG. 6c shows a top view of the biopsy needle 78 when top ribbon 80 is withdrawn to form opening 91 therein, while the left most illustration of FIG. 6b is a end view of the maximum opening 91 in needle 78. The center illustration of FIG. 6b shows top ribbon 80 as it moves to partially close opening 91 while cutting the tissue sample received in the lumen of needle 78 from the remaining prostate tissue.

Figure 6D:
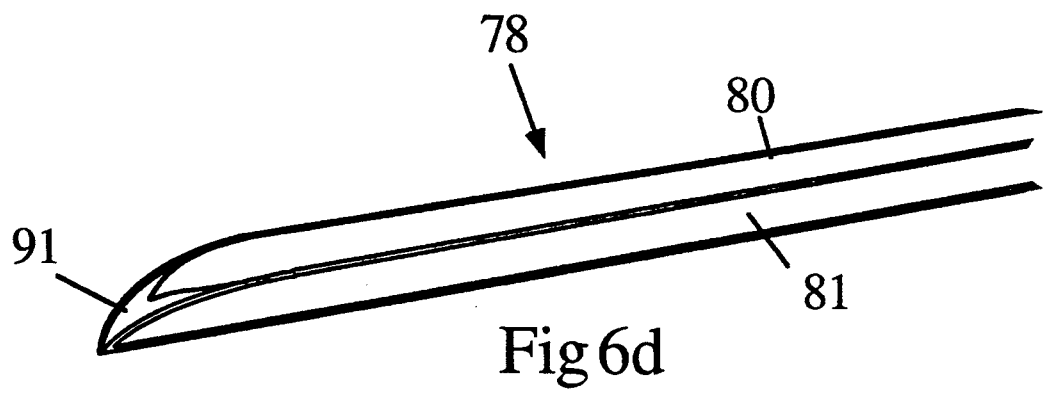
FIG. 6d is a side perspective of the biopsy needle as shown in FIG. 6c as the cutting procedure progresses.

FIG. 6d is a side perspective of needle 78 as top ribbon 80 has moved to almost complete the severing of the tissue sample and close opening 91 in needle 78, while the illustration at the extreme right of FIG. 6b shows a front end view of needle 78 when top ribbon 80 has progressed to the point shown in FIG. 6d.

Another alternative form of the biopsy needle of the present invention is embodied as a permanently curved needle, as illustrated in FIGS. 7a–7e. This embodiment necessitates that the orifice point 45 from which the needle emerges must be able to translate in the longitudinal plane of probe 10. The reason is that the needle path is a segment of a circle, therefore, since tumors at different depths would necessitate varying segments to reach them, the entrance point must be controlled in order to ensure that the arc intersects the proper point.

As illustrated, curved needle 92 is attached at its inner end to flexible passageway 55 and slidable disposed through a positioning block 92 fixed within slaved biopsy probe 10 to exit at portal orifice 45. In operation, the ultrasonic receiver 32 aligns the gimbaled head 12 of probe 10 to the scan disk in which the tumor falls in the same manner as that described hereinbefore in reference to the other embodiments. Positioning block 92 is then moved by computer controls 47 to place orifice 45 at a point such that the arc of the circle through which the tip of curved biopsy needle 92 moves will intersect the center of the identified tumor 35. Three different tumor locations are illustrated in respective FIGS. 7a–7c, with the fully retracted position of the curved needle 92 being shown in FIG. 7d. The mechanism for taking the tissue sample is as described in the previous embodiments. The ultrasonic receiver 32 is not annular in this embodiment since curved needle 92 emerges from a point below the receiver.

In each of the described embodiments, after the deployed biopsy needle (or treatment conduit) has been retracted out of the prostate, through the rectal wall 29, and into probe 10, it can be withdrawn via the rotary selector, or instrument cylinder 60 and associated instrument passageway, from the probe 10. The rotary selector 60 may then access an electric resistance heater, (one of the functional elements 67 described hereinbefore in reference to FIG. 2) which is then passed through the system until the tip emerges from orifice 45 and comes in contact with rectal wall 29. Localized heating or a similar technique is then used to produce scar tissue blocking the exit wound in the rectal wall 29. Once the sealing device is, in turn, withdrawn from probe 10, passageway 55 can be used to conduct topical antibiotics to the area in the same manner.

Figure 7A:
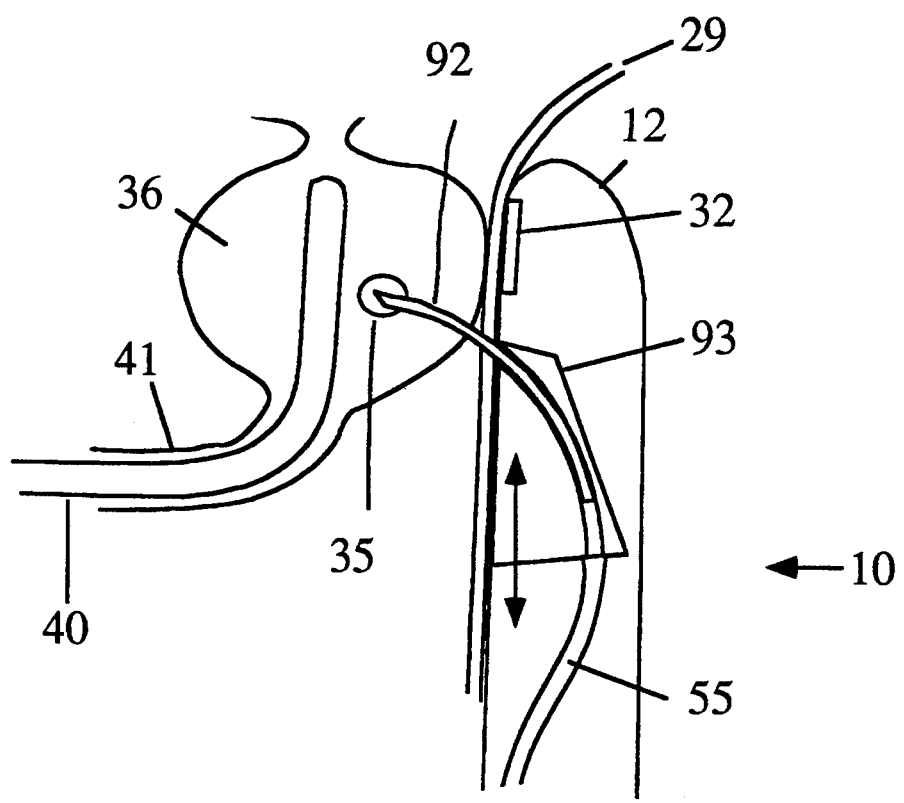
FIG. 7a-7c are part sectional, part schematic, views of a curved biopsy needle employed in the present invention to reach tumors at diverse locations within the prostate.
Figure 7B:
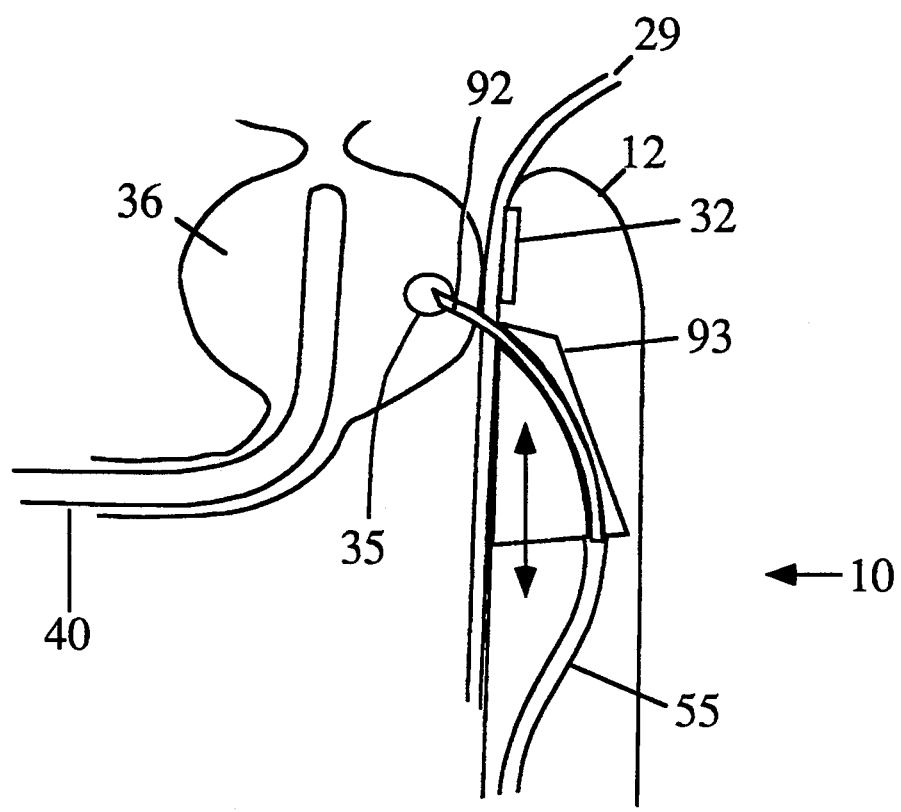
Figure 7C:
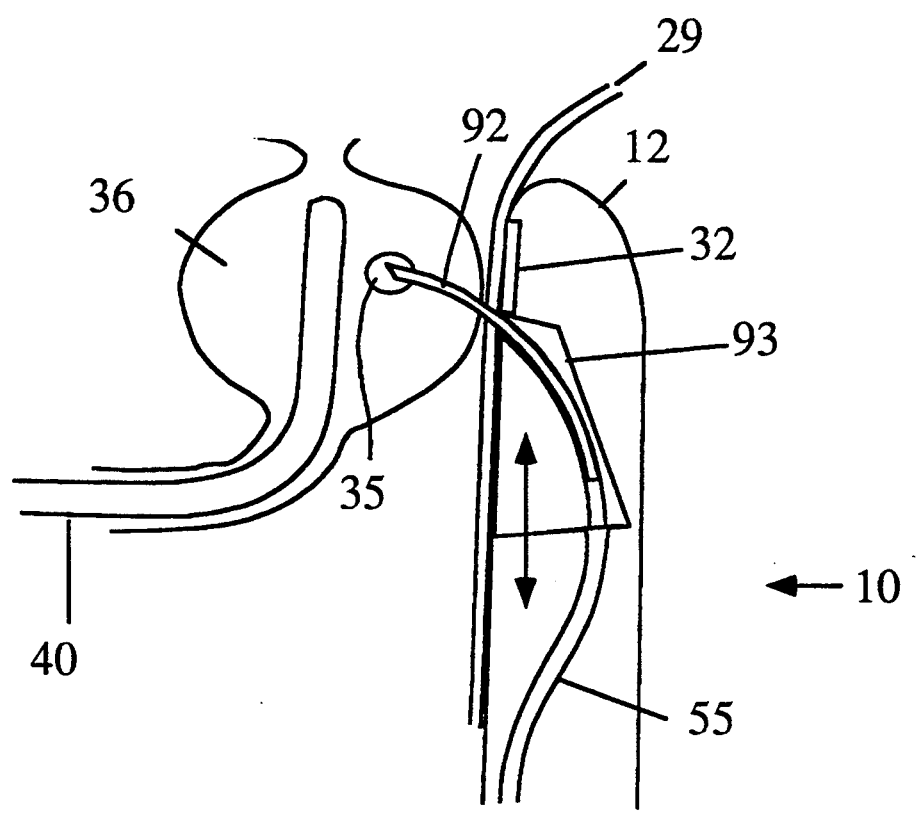
Figure 7D:
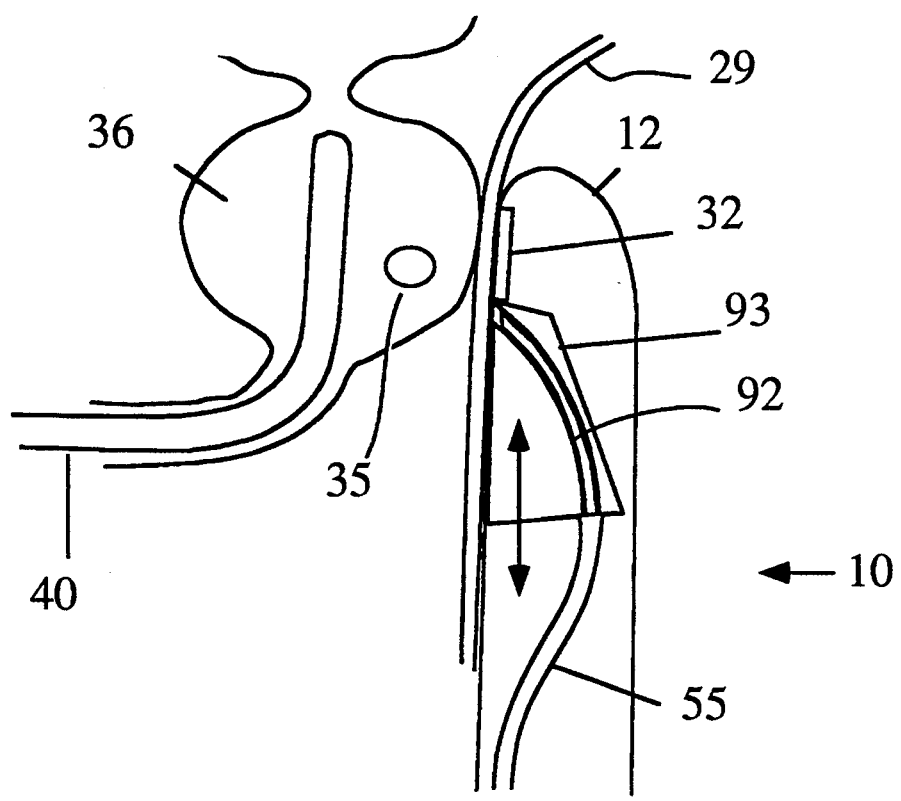
FIG. 7d is a part sectional, part schematic view of the curved biopsy needle shown in FIGS. 7a-7c when in the fully retracted position.
Figure 7E:
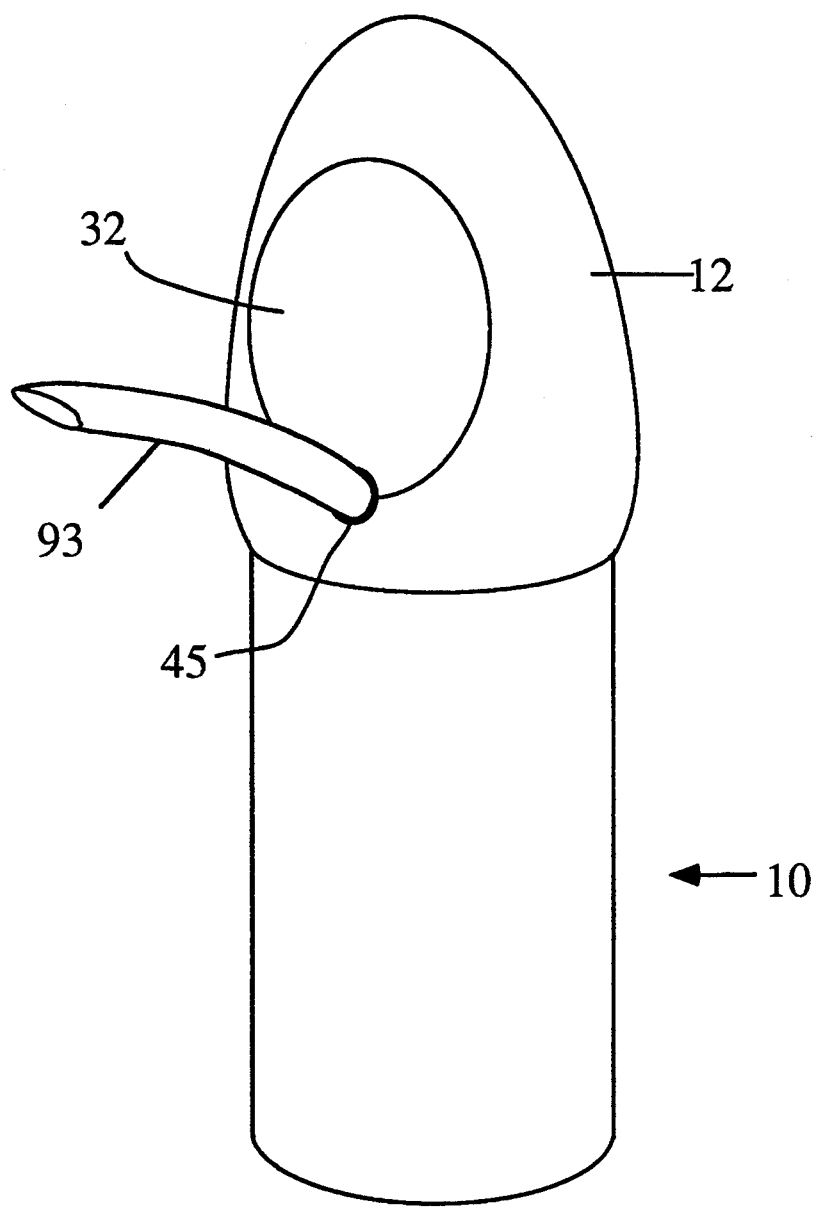
FIG. 7e is a part sectional side perspective of the slaved biopsy probe of the present invention when employing the curved biopsy needle shown in FIGS. 7a-7d.
Figure 8A:
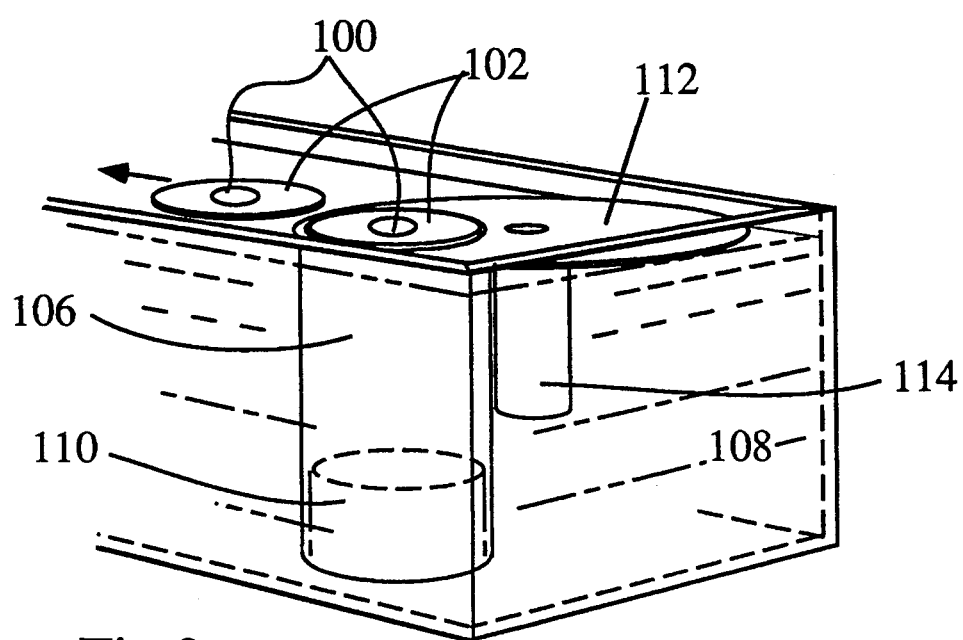
FIG. 8a is a part sectional, part schematic, perspective, view of a sample cutting system for analysis of the tissue sample taken by the slaved biopsy system of the present invention.
Figure 8B:
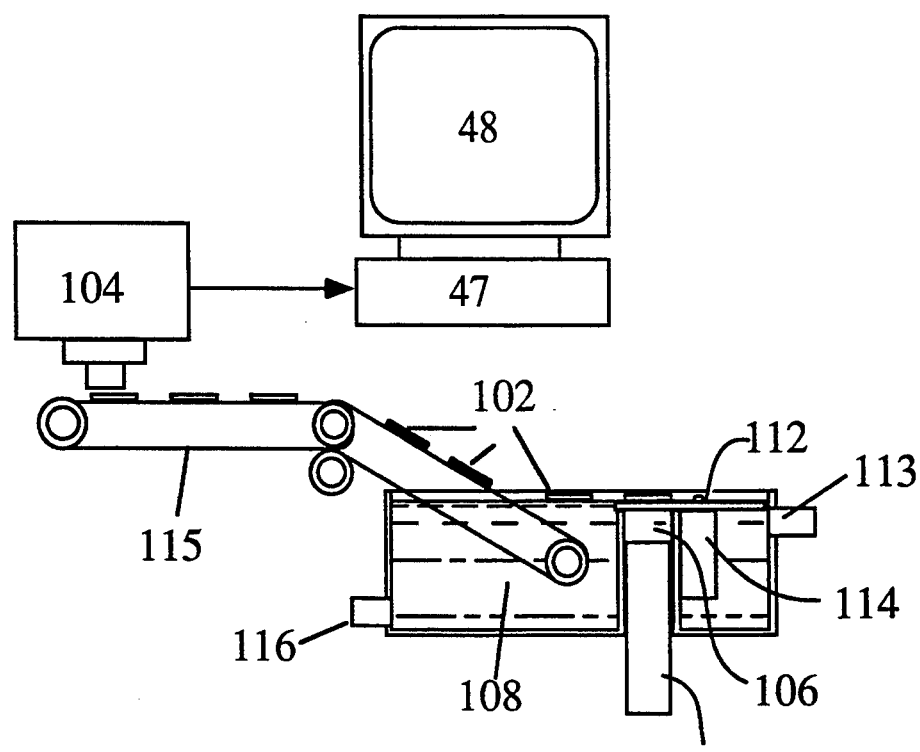
FIG. 8b is a part sectional, part schematic side view of the sample cutting system shown in FIG. 7a and illustrating the automated sample transportation, computer analysis, and display portion for analyzing the cut tumor tissue sample.
Figure 8C:
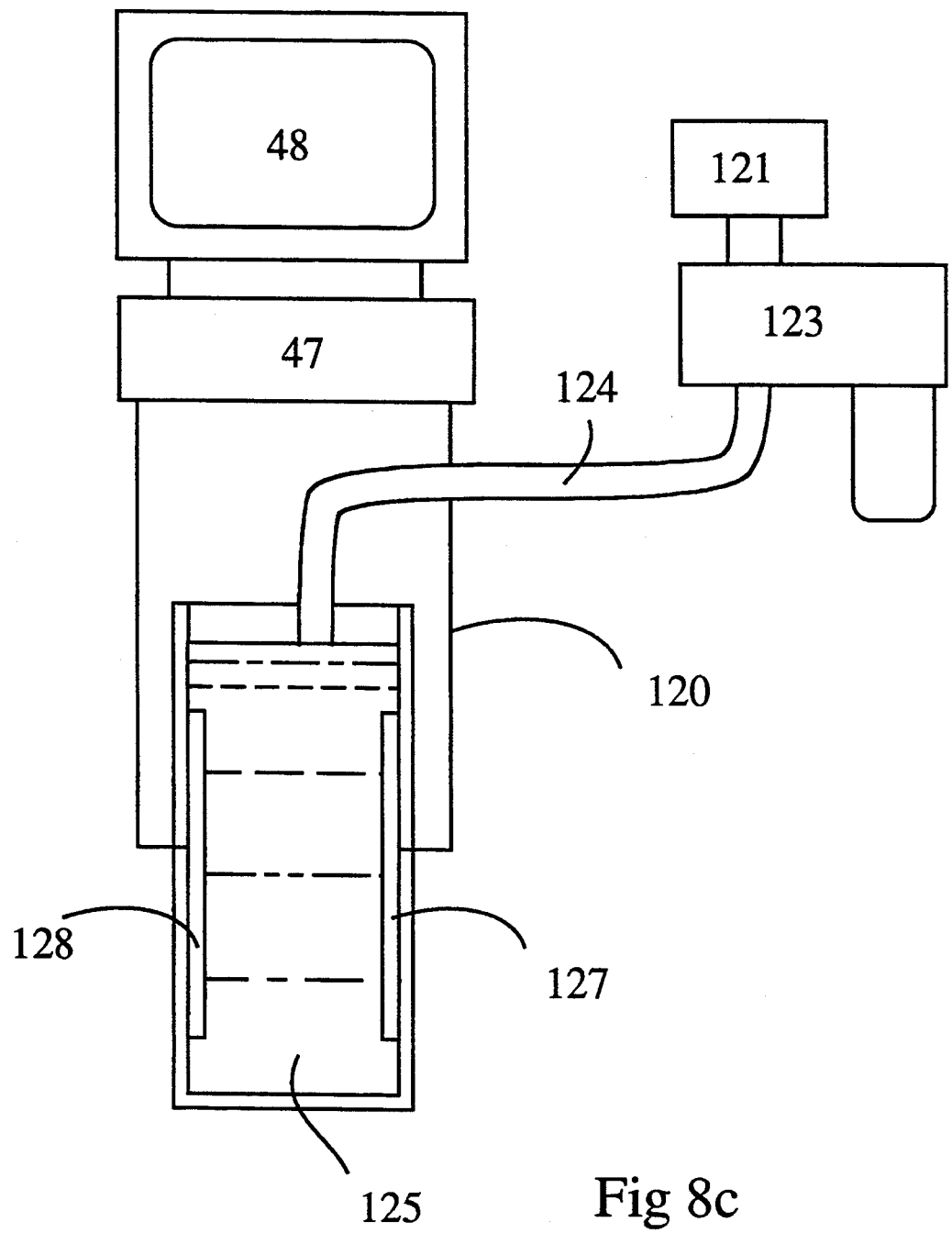

Referring now to FIGS. 8a–8c, the apparatus and procedure for automated processing of the extracted biopsy tissue sample will now be described. An optical examination system and procedure is illustrated in FIGS. 7a and 7b wherein the tissue sample 100 is sectioned into a number of thin slices 102 which are presented on a substrate to a built-in microscope fitted with a miniature video camera 104. Video equipped microscopes of this type are commercially available and may be integrated with the system computer 47 to acquire, and display, the image on the built-in display screen 48. Alternately, the image may be transferred to a remote display or transmitted via electronic mail to a pathology laboratory for analysis. When the image is to be analyzed on site, the on-line data base network of the patented prostate examination system referred to hereinbefore can be used to access images of known tumors for comparison purposes.

When acquired, the tissue sample 100 is deposited in a chamber 106 containing a gel material (not designated) therein that is in the liquid state by virtue of the fact that it is held at approximately 100 degree F by a surrounding water bath contained in a tank 108. The water temperature in tank 108 is controlled by a flow of water therethrough via a suitable water inlet and water outlet, as designated respectively, by reference numerals 113 and 116. Once tissue sample 100 is immersed in the fluid gel, the temperature of chamber 106 is lowered, by changing the flow of water through tank 108 to cool water, causing the gel to solidify. The collagen based hydro-gels employed solidify or gel when the temperature thereof drops slightly below 100 degrees F. Once the gel is solidified, the tissue sample 100 is held in the rubbery matrix.

In lieu of the gel material, paraffin wax may be employed in chamber 106, requiring slightly higher temperature in tank 108 for liquification thereof.

The bottom of chamber 106 is formed by the upper face of a moveable ram 110. Ram 110 is employed to incrementally push the gel mass with the enclosed tissue sample 100 out the top of chamber 106. As the gel material is extruded from the top of chamber 106, a rotating microtome knife 112, driven by motor 114, cuts successive slices 102 from the mass. The cold water flow in tank 108 floats the detached slices 102 away from the gel mass. The floating thin slices 102 are collected, one at a time, on a ribbon of mylar film 115 which emerges at an angle from the surface of the water flow and is moving in the same direction as the flow. The thin tissue slices 102 are then transported by the ribbon 115 to the focal point of microscope 104 where they are illuminated and imaged. The images are enlarged and enhanced in the computer 47 and are then displayed on the computer screen 48 in succession.

The operating physician has the option of making the diagnosis at that time, or the images may be forwarded electronically to a remotely located pathologist for further examination and/or diagnosis.

Referring now to FIG. 8 an ultrasonic density examination system for analyzing suspect tissue specimens is shown, and designated generally by reference numeral 120. Examination system 120 makes use of the fact that there are differences in the ultrasonic characteristics of malignant and nonmalignant tumors at various frequencies. Once a tissue sample is extracted by the slaved biopsy probe 10, the sample is deposited in a receiving chamber 121 where it is broken up into individual cells by a macerator 123 with water being added thereto to make a cell suspension. This suspension is then transferred, via conduit 124, to an ultrasonic chamber 125 and subjected to a swept-frequency ultrasonic field transmitted from a large transducer 127 on one side of chamber 125 and received by a matching transducer 128 on the opposite side of ultrasonic chamber 125. The density and absorption characteristics of the sample cells are measured at different frequencies and the results compared to a look-up table containing values derived from samples of known malignancies by computer 47. The results of the comparisons and any noted similarities are displayed on the computer display screen 48 for the operating physician to use in evaluating the data and making the diagnosis. These results also would be automatically archived by the base computer, along with all patient data and direct difference comparisons with historical data from the individual patient being evvaluated, as in the patented system referred to hereinbefore.

The present invention will also permit the use of a recently developed diagnostic system which uses laser induced florescence to differentiate between malignant and non-malignant tumors. By deploying a fiber optic borne laser illuminator through an instrument conduit as described herein, this technique could allow real time, on site diagnosis, thus permitting immediate, appropriate treatment during a single doctor-patient interaction.

The virtues of the above described invention over conventional biopsy needle and analysis systems include; precise placement of the biopsy tube to take the tissue sample exactly where the physician wants (i.e. at the core of the tumor), control over the size of the tissue sample obtained, the ability to characterize the tissue sample while the biopsy probe is still in place, the ability to immediately deliver potent treatment modalities as described, the ability to clean and seal the exit wound to prevent infection, and the patient comfort features. Thus, the present invention maximizes both patient comfort and the precise extraction of tissue samples from the area of interest without the accessibility problems encountered by prior art systems, and provides the means to employ advanced new treatment options. Accordingly, these and other features of the present invention should have a major impact on the number of false negatives now experienced when employing current biopsy sampling procedures.

No specific materials have been discussed herein for most of the component parts of the invention, it being understood that, where no materials are mentioned, any metal, alloy, plastic or composite material suitable for the purposes intended is considered applicable for constructing the component parts of the invention. Also, various conduits, motors, actuators, reservoirs, and the like, have not been described in detail in the interest of brevity and clarity, it being understood that where such conventional features are needed, they are intended to be included in the specific examples described herein.

Although the invention has been described relative to specific embodiments thereof, it is not so limited and there are numerous variations and modifications of the invention that will be readily apparent to those skilled in the art in the light of the above teachings.

It is therefore to be understood that, within the scope of the appended claims, the invention may be practiced other than as specifically described herein.

What is claimed as new and desired to be secured by Letters Patent of the United States is:

1. In combination with an ultrasonic system for detecting, identifying and precisely locating tumors in the prostate gland of a patient and including, a control computer positioning and removal mechanism for a ultrasonic transmitter carried by a urethral probe, and a control computer screen visible to the medical personnel utilizing the system, the improvement therewith consisting of:

a computer controlled biopsy system for taking a biopsy of the located tumor;

said biopsy system including a rectal probe movable by and controlled by the computer;

said rectal probe positionable within the rectum of the patient having the suspected tumor;

said rectal probe housing a biopsy needle;

ultrasonic receiver means carried by said rectal probe for receiving ultrasonic signals from the ultrasonic transmitter carried by the urethral probe;

said ultrasonic receiver means carried by said rectal probe assisting in, and serving to indicate, alignment of said biopsy needle with the tumor;

means for extending said biopsy needle from said rectal probe and inserting said biopsy needle through the rectum wall into the prostate to enter and take a tissue sample from the center of the detected tumor; and means for retracting the biopsy needle and contained tissue sample from the patient for analysis while leaving the urethral and rectal probes intact.

2. The combination of claim 1 including at least one optical lens carried by, and disposed adjacent to an opening in, said rectal probe to provide visual images of the rectal wall;

said optical lens being in communication with the control computer screen to provide visual images of the rectal wall to the medical personnel employing said biopsy system; and means for rotating said rectal probe to permit placement of said optical lens at the desired angular relationship within the rectum.

3. The combination of claim 1 including lubricant and anesthetic ports in said rectal probe to dispense lubricant and facilitate insertion of said rectal probe in the rectum and to dispense an anesthetic cleanser to anesthetically wash down the rectal wall area to be penetrated by said biopsy needle.

4. The combination of claim 1 including means carried by said rectal probe to seal the exit hole made by the biopsy needle upon withdrawal of said needle from the rectal wall; and, means for dispensing an antibiotic to the sealed area to minimize the possibility of infection.

5. The combination of claim 1 wherein said rectal probe includes a gimbaled tip end portion; said biopsy needle being positioned within said gimbaled tip end portion; and means for manipulating the vertical angle of said gimbaled tip end portion to align said needle with the detected tumor.

6. The combination of claim 1 wherein said ultrasonic receiver means carried by said rectal probe comprises a convex wedge shaped plug member; said convex wedge shaped plug member also serving as a closure for the tip of said biopsy needle and as a penetrating point for said biopsy needle; and means for extending and withdrawing said convex wedge shaped plug member within said biopsy needle to expose a tubular cutting edge at the tip of said needle for cutting and removal of a sample of tissue from the detected tumor.

7. The combination of claim 6 wherein said biopsy needle is constructed of a memory material tube;

a tubular conduit for housing said biopsy needle and providing communication therewith with computer controls;

a curved passageway formed in said tubular conduit; said tubular conduit having a distal end connecting said curved passageway to an exit portal in said rectal probe and a proximal end in communication with a rotary instrument selection cylinder disposed within said rectal probe.

8. The combination of claim 7 including an annular heating element surrounding said tubular conduit at the distal end thereof;

said biopsy needle being maintained in the shape of said curved passageway in the retracted position and, upon command, being pushed out of said exit portal while being heated by said annular heating element to assume a straight, rigid, condition.

9. The combination of claim 8 including an internal heating element disposed within said biopsy needle to maintain the elevated temperature thereof achieved by the heat from said annular heating element when said biopsy needle exits said anal probe and penetrates the rectal wall.

10. The combination of claim 9 wherein said tubular conduit is slidably connected to a top center port in said rotary instrument selection cylinder;

said rotary instrument selection cylinder having an elongated S-curve shaped passageway extending therethrough from said top center port to an opening adjacent the periphery of said rotary instrument selection cylinder, to thereby provide an off-set interface between the instrument passageway and a series of instrument feed tubes;

said instrument feed tubes slidably interfacing with the lower face of said rotary instrument selection cylinder to provide selective functional elements access to the tumor of the patient.

11. The combination of claim 10 including said tubular biopsy needle extending through said tubular conduit, said rotary instrument cylinder and one of said instrument feed tubes, and protruding into a drive mechanism;

said drive mechanism serving to selectively drive said needle forward into the tumor or back to withdraw said needle through the instrument feed tube to recover the tissue sample obtained thereby; and to clear the way for the deployment of other instruments through said passageway.

12. The combination of claim 11 including said convex wedge shaped plug for said tubular needle being provided with an integral cable extending completely through the lumen of said tubular biopsy needle and also engaging a plug control capstan/idler wheel drive mechanism, said convex wedge shaped plug being movable with said tubular biopsy needle forward, and independently movable forward and backward, by said plug control capstan/idler wheel mechanism to first, clear the lumen of said tubular biopsy needle to permit taking of the tissue sample and second, to completely withdraw said convex edge shaped plug through its designated instrument feed tube to permit access to the tissue sample for evaluation.

13. The combination of claim 1 wherein said biopsy needle comprises an extruded triangular needle formed of three separate stainless steel ribbons;

each of said separate stainless steel ribbons being wound onto an individual spool;

a support structure having said individual spools mounted thereon in a spaced 120 degree angular relationship;

means for simultaneously rotating said spools to deploy and retract said separate stainless steel ribbons;

a swaging die receiving said separate ribbons as deployed from said spools and serving to interlock the ribbon edges to form a rigid triangular needle structure;

a triangular shaped needle tip provided in said swaging die and connected to each of said separate ribbons;

a flexible tube in communication with said triangular shaped needle tip;

said flexible tube being in connection with a vacuum device disposed external to said rectal probe; and said vacuum device serving to aspirate the tissue sample obtained by said biopsy needle to an analysis station.

14. The combination of claim 13 wherein said three separate stainless steel ribbons are provided with sharp leading edges and welded together to form said triangular shaped needle tip;

said needle tip having an open beveled end and disposed within said swaging die;

said open end of said triangular shaped needle tip being closed by an exposed beveled cutting plug slidably received therein;

said exposed beveled cutting plug having a tapered face disposed flush with the beveled ends of said three stainless steel ribbons;

said beveled cutting plug including a trough depression disposed aft of the tapered face thereof; whereby, when said beveled cutting plug is extended beyond the beveled ends of said three stainless steel ribbons to expose said trough depression, the surrounding tumor tissue bulges into and fills said trough depression; and when said beveled cutting plug is retracted back into said needle the tumor tissue in said trough depression is sheared off by said sharp beveled ends of said stainless steel ribbons for aspiration by said vacuum device.

15. The combination of claim 1 wherein said biopsy needle comprises an extruded triangular needle formed of three separate stainless steel ribbons;

each of said separate stainless steel ribbons being wound onto separate individual spools;

a support structure having said individual spools mounted thereon at 120 degree spaced intervals;

means for rotating said spools to individually deploy and retract said separate stainless steel ribbons;

two members of said separate stainless steel ribbons being provided with tapered end surfaces along a free edge thereof and the other edge of each of said two members of said separate stainless steel ribbons being straight and joined to each other;

said free edges of said two members of said separate stainless steel ribbons forming a track for receiving and guiding the third of said separate stainless steel ribbons;

said third member of said stainless steel ribbons having an end surface that closes the tapered end surface of said two members of said stainless steel ribbons to form a tapered tip for said biopsy needle;

said third member of said stainless steel ribbons being retractable a distance from said two members of said stainless steel ribbons to expose an open end needle to cut and remove a tissue sample from the detected tumor;

said third member of said stainless steel ribbons being again deployed to close the tip end of said biopsy needle and capture the cut tissue sample therein.

16. The combination of claim 1 wherein said rectal probe includes a gimbaled tip end portion and said ultrasonic receiver means is supported by said gimbaled tip end portion;

said biopsy needle comprising a permanently curved needle that moves in a path constituting an arc of a circle;

said curved needle having an inner end secured to a flexible passageway supported by said rectal probe;

a computer controlled positioning block carried by said rectal probe and slidably receiving said curved needle therethrough; whereby said ultrasonic receiver means aligns said gimbaled tip end portion with the detected prostate tumor and the computer controls linearly moves said positioning block to a point wherein the tip of said curved biopsy needle will move in an arc of a circle that penetrates the center of the detected tumor.

17. A system for obtaining a biopsy of a prostate tumor comprising, in combination:

a urethral probe for ultrasonically detecting and locating the position of a tumor within a prostate capsule;

computer means connected to said urethral probe and including a computer screen for displaying an image and relative location of the prostate tumor;

a rectal probe containing a biopsy needle;

said computer means being also connected to said rectal probe and said computer screen displaying an image of said rectal probe relative to said urethral probe;

ultrasonic receiver means carried by said rectal probe for aligning said biopsy needle with the prostate tumor;

means for extending said biopsy needle from said rectal probe to the prostate tumor and for taking a biopsy tissue sample therefrom; and means for retracting the biopsy needle and tumor tissue sample through said rectal probe to an analysis station.

18. The combination of claim 17 including an optical interpretation system for processing of the tumor tissue sample taken by said biopsy needle;

said optical interpretation system including a tissue receiving chamber for receiving the tumor tissue sample;

said tissue receiving chamber containing a quantity of a meltable material therein;

a temperature controlled water bath surrounding said tissue chamber;

means for maintaining said meltable material in a melted liquid state when said tumor tissue sample is received therein, and permitting cooling of said meltable material to cause said meltable material to become a solidified matrix after receipt of said tumor tissue sample;

a movable ram disposed at the bottom of said tissue receiving chamber;

said movable ram serving to incrementally push the solidified mass toward the top of said tissue receiving chamber;

a rotating microtome knife assembly disposed at the top of said tissue receiving chamber and serving to cut successive thin sample slices from the solidified mass as said ram moves said mass upward;

means for individually transporting each successive slice to an observation site;

a microscope at the observation site and having a focal point for illuminating and imaging the individual sample slices;

said computer means serving to enlarge and enhance the sample slice images; and said computer screen displaying the enlarged and enhanced images for observation and interpretation by the attending medical personnel.

19. The combination of claim 18 wherein said temperature controlled water bath is provided with a water inlet and a water outlet;

said water inlet and said water outlet permitting continuous water flow therein whereby hot water flow raises the temperature of the water bath and contained tissue receiving chamber to a temperature maintaining the contained meltable material in the liquid state until the tumor tissue sample is deposited therein; and a flow of cold water causes the water bath and contained tissue chamber to drop to a temperature effecting solidification of the meltable material after the tumor tissue sample has been received therein.

20. The combination of claim 17 including an ultrasonic density examination system for processing the tumor tissue sample taken by said biopsy needle;

said ultrasonic examination system including a tumor tissue receiving chamber;

a macerator containing a quantity of water receiving the tumor tissue sample from said tumor tissue receiving chamber and forming a cell suspension of the tumor tissue sample;

an ultrasonic chamber receiving the tumor tissue sample cell suspension from said macerator;

a first ultrasonic transducer on one side of said ultrasonic chamber and a second matching ultrasonic transducer on the opposite side of said ultrasonic chamber; whereby said first ultrasonic transducer transmits a swept-frequency ultrasonic field through said ultrasonic chamber with said swept-frequency ultrasonic field being received by said second ultrasonic transducer and indicating the density and absorption characteristics of said tumor tissue sample in said ultrasonic chamber at the different frequencies, and said computer and computer screen indicate the comparison and similarities of said density and absorption characteristics with known malignancies for evaluation by the attending medical personnel.

21. A method of obtaining and analyzing a biopsy of a prostate tumor comprising the steps of:
(a) providing a urethral probe for ultrasonically detecting and locating the position of a suspected tumor within a prostate capsule;
(b) providing a slaved biopsy probe housing an ultrasonic receiver and a biopsy needle;

employing the ultrasonic receiver to precisely locate the suspected prostate tumor and align the biopsy needle therewith;
(c) extruding the biopsy needle from the biopsy probe to penetrate the rectal wall and extend into the suspected tumor;
(d) extracting a tissue sample from the suspected tumor with the biopsy needle;
(e) while leaving the biopsy needle within the suspected tumor, extracting the tissue sample therefrom to an analysis station; and,
(f) analyzing the tissue sample to determine if the tissue sample is malignant.

22. The method of claim 21 including performing each of steps (a) through (f) under the control of a computer.

23. The method of claim 22 including the step of providing treatment directly to the prostate tumor via the rectal probe after it is determined that the tumor is malignant.

24. The method of claim 23 wherein the treatment provided directly to the prostate tumor is selected from the group of tumor treatments selected from the group of treatments consisting of thermal, surgical, chemical, radiological, high energy and cryogenics.

25. The method of claim 21 wherein the step of analyzing the tissue sample includes an optical analysis procedure and including the steps of:
depositing the tissue sample in a container of a liquid gel material;
employing an elevated temperature water bath for maintaining the gel in a liquid state until the tissue sample is received therein;
reducing the temperature of the water bath to cause the gel to solidify into a rubbery matrix containing the tissue sample;
incrementally slicing thin slices of the solidified gel containing the tissue sample;
transporting the thin slices to an observation site;
providing a microscope at the observation site having a focal point for illuminating and imaging the individual sample slices;
employing the computer to enlarge and enhance the sample slice images and make comparisons of the enhanced images with known maliginances;
utilizing the comparison results by displaying onto the computer screen for viewing and utilization by attending medical personnel; and
selectively, data link conveying the comparision results to remote locations for interpretation by other medical personnel.

26. The method of claim 21 wherein the step of analyzing the tissue sample includes an ultrasonic analysis procedure and including the steps of:
depositing the tissue sample in a tumor tissue receiving chamber;
transferring the tissue sample from the tissue receiving chamber to a macerator containing a quantity of water therein;
macerating the tissue sample to form a cell suspension of the tumor tissue sample;
transferring the cell suspension of the tumor tissue sample to a ultrasonic chamber;
providing a first ultrasonic transducer on one side of the ultrasonic chamber;
providing a second ultrasonic transducer on the opposite side of the ultrasonic chamber;

employing the first ultrasonic transducer to transmit a swept-frequency ultrasonic field through the cell suspension contained in the ultrasonic chamber and received by the second ultrasonic transducer;

employing a computer to determine the density and absorption characteristics of the tumor tissue cell suspension in the ultrasonic chamber at the different frequencies;

employing a computer screen to indicate the comparison and similarities of the density and absorption characteristics of the tissue sample cell suspension with known malignancies for evaluation by the attending medical personnel; and providing automatic archiving of the patient data obtained along with direct difference comparisons with historical data from the individual patient being evaluated.

* * * * *